United States Patent
Alonso-Alija et al.

(10) Patent No.: US 7,115,602 B2
(45) Date of Patent: Oct. 3, 2006

(54) HETEROCYCLES 3

(75) Inventors: Cristina Alonso-Alija, Haan (DE); Heike Gielen, Leverkusen (DE); Martin Hendrix, Odenthal (DE); Ulrich Niewöhner, deceased, late of Wermelskirchen (DE); by Maria Niewöhner, legal representative, Wermelskirchen (DE); Dagmar Schauss, Solingen (DE); Hilmar Bischoff, Wuppertal (DE); Nils Burkhardt, Düsseldorf (DE); Volker Geiss, Ratingen (DE); Karl-Heinz Schlemmer, Wuppertal (DE); Nigel J. Cuthbert, Bucks (GB); Mary F. Fitzgerald, Yarton (GB); Graham Sturton, Bray Maidenhead (GB)

(73) Assignee: Bayer Aktiengesellschaft, Leverkusen (DE)

( * ) Notice: Subject to any disclaimer, the term of this patent is extended or adjusted under 35 U.S.C. 154(b) by 370 days.

(21) Appl. No.: 10/160,352

(22) Filed: May 30, 2002

(65) Prior Publication Data

US 2003/0139415 A1 Jul. 24, 2003

(30) Foreign Application Priority Data

Jun. 1, 2001 (GB) .......................... 0113344.6

(51) Int. Cl.
*A01N 43/64* (2006.01)
*A61K 31/53* (2006.01)
*C07D 487/00* (2006.01)

(52) U.S. Cl. .................... 514/243; 544/184
(58) Field of Classification Search ................ 514/183, 514/242, 243; 544/180, 184
See application file for complete search history.

(56) References Cited

U.S. PATENT DOCUMENTS

| | | | |
|---|---|---|---|
| 3,840,537 A | 10/1974 | Garside et al. | 260/249.5 |
| 3,941,785 A | 3/1976 | Clarke et al. | 260/249.5 |
| 4,278,673 A * | 7/1981 | Hartely et al. | 424/249 |
| 6,362,178 B1 | 3/2002 | Niewohner et al. | 514/218 |

FOREIGN PATENT DOCUMENTS

| | | |
|---|---|---|
| DE | 2255172 | 5/1973 |
| DE | 2364076 | 7/1974 |
| DE | 2811780 | 9/1978 |
| EP | 1092719 | 4/2001 |
| WO | 9924433 | 5/1999 |
| WO | 9967244 | 12/1999 |

OTHER PUBLICATIONS

Granata et al,PubMed Abstract 12876405, also cited as Int. Arch. Allergy. Immunol., 131/3,153–63(2003).*
Scott et al, Pubmed Abstract 12783578, also cited as Expert Opin. Ther. Targets, 7/3,427–40(2003).*
Giembycz MA., PubMed Abstract 11772257, also cited as Expert Opin. Investig. Drugs,10/7,1361–79(2001).*
Strurton, et al, PubMed Abstract 12010850, also cited as Chest, 121/5, 192S–196S(2002).*
Jacob et al, PubMed Abstract 12185965, also cited as Therapie, 57/2,163–8(2002).*
Barnette, M., "PDE 4 Inhibitors in Asthma and Chronic Obstructive Pulmonary Disease (COPD)" Progress in Drug Research, 53: 193–229 (1999).
Dyke, H., Montana, J., "The Therapeutic Potential of PDE4 Inhibitors", Exp. Opin. Invest. Drugs, 8: 1301–1325 (1999).
Duplantier, A., Biggers, M., Chambers, R., Cheng, J., Cooper, K., Damon, D., Eggler, J., Kraus, K., Marfat, A., Masamune, H. Pillar, J., Shirley, J., Umland, J., Watson, J., "Biarylcarboxylic Acids and —amides: Inhibition of Phosphodiesterase Type IV Versus [$^3$H]Rolipram Binding Activity and Their Relationship to Emetic Behavior in the Ferret", J. Med. Chem., 39; 120–125 (1996).

* cited by examiner

*Primary Examiner*—James O. Wilson
*Assistant Examiner*—Zachary C. Tucker

(57) ABSTRACT

The invention relates to 7-(4-tert butyl-cyclohexyl)-imidazotriazinones, processes for their preparation and their use in medicaments, esp. for the treatment and/or prophylaxis of inflammatory processes and/or immune diseases.

13 Claims, No Drawings

HETEROCYCLES 3

The invention relates to 7-(4-tert butyl-cyclohexyl)-imidazotriazinones, processes for their preparation and their use in medicaments, esp. for the treatment and/or prophylaxis of inflammatory processes and/or immune diseases.

Phosphodiesterases (PDEs) are a family of enzymes responsible for the metabolism of the intracellular second messengers cAMP (cyclic adenosine monophosphate) and cGMP (cyclic guanosine monophosphate). PDE 4, as a cAMP specific PDE, catalyses the conversion of cAMP to AMP and is the major if not sole isoform of the phosphodiesterase enzymes present in inflammatory and immune cell types. Inhibition of this enzyme leads to the accumulation of cAMP which, in these cells, leads to the inhibition of a range of pro-inflammatory functions. Uncontrolled production of inflammatory mediators can lead to acute and chronic inflammation, tissue damage, multi-organ failures and to death. Additionally, elevation of phago-cyte cAMP leads to inhibition of oxygen radical production. This cell function is more sensitive than others such as aggregation or enzyme release.

It is now recognised that both asthma and COPD (Chronic obstructive pulmonary disease) are chronic inflammatory lung diseases. In the case of asthma the eosinophil is the predominant infiltrating cell. Subsequent release of superoxide radicals as well as damaging cationic proteins from these infiltrating cells are believed to play a role in the progression of the disease and development of airway hyper-reactivity.

By contrast, in COPD the neutrophil is the predominant inflammatory cell type found in the lungs of sufferers. The action of mediators and proteases released in the environment of the lung is believed to result in the irreversible airway obstruction seen in COPD. In particular the action of proteases in degrading the lung matrix results in fewer alveoli and is likely to be the major cause of accelerated long term lung function decline seen in this disease.

Treatment with a PDE 4 inhibitor is expected to reduce the inflammatory cell burden in the lung in both of these diseases [M. S. Barnette, "PDE 4 inhibitors in asthma and chronic obstructive pulmonary disease", in: Progress in Drug Research, Birkhäuser Verlag, Basel, 1999, pp. 193–229; H. J. Dyke and J. G. Montana, "The therapeutic potential of PDE 4 inhibitors", Exp. Opin. Invest. Drugs 8, 1301–1325 (1999)].

While PDE 4-inhibitors also usually produce side effects like vomiting, it has been shown that these side effects correlate with the affinity to a high affinity binding site for rolipram, and that emesis is reduced in compounds with a decreased affinity to this binding site (J. Med. Chem. 1996, 39, 120–125).

WO 99/24433 and WO 99/67244 describe 2-phenyl-imidazotriazinones as synthetic intermediates for the synthesis of 2-(aminosulfonyl-phenyl)-imidazotriazinones as inhibitors of cGMP-metabolizing phosphodiesterases.

U.S. Pat. No. 4,278,673 discloses 2-aryl-imidazotriazinones with cAMP phosphodiesterase inhibitory activity for the treatment of i.a. asthma.

The present invention relates to compounds of the general formula (I)

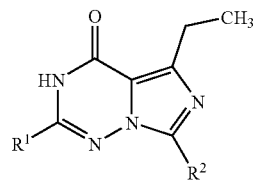

in which
$R^1$ denotes $(C_6-C_{10})$-aryl, which is optionally substituted by identical or different residues selected from the group consisting of halogen, $(C_1-C_4)$-alkyl, trifluoromethyl, cyano, nitro und trifluoromethoxy, or
denotes $(C_1-C_8)$-alkyl, which is optionally substituted by 3- to 10-membered carbocyclyl, or
denotes 3- to 10-membered carbocyclyl, which is optionally substituted by identical or different $(C_1-C_4)$-alkyl residues, and
$R^2$ denotes 4-tert-butyl-cyclohex-1-yl, Another embodiment of the invention relates to compounds of the general formula (I), in which
$R^1$ denotes naphthyl, or
denotes phenyl, which is optionally substituted by identical or different halogen atoms and
$R^2$ has the meaning indicated above.

Another embodiment of the invention relates to compounds of the general formula (I), in which $R^1$ has the meaning indicated above, and $R^2$ denotes cis-4-tert-butyl-cyclohex-1-yl.

The compounds according to this invention can also be present in the form of their salts, hydrates and/or solvates.

In general, salts with organic or inorganic bases or acids may be mentioned here.

Physiologically acceptable salts are preferred in the context of the present invention.

Physiologically acceptable salts can also be salts of the compounds according to this invention with inorganic or organic acids. Preferred salts are those with inorganic acids such as, for example, hydrochloric acid, hydrobromic acid, phosphoric acid or sulphuric acid, or salts with organic carboxylic or sulphonic acids such as, for example, acetic acid, maleic acid, fumaric acid, malic acid, citric acid, tartaric acid, ethanesulphonic acid, benzenesulphonic acid, toluenesulphonic acid or naphthalene-disulphonic acid. Preferred pyridinium salts are salts in combination with halogen.

The compounds according to this invention can exist in stereoisomeric forms which either behave as image and mirror image (enantiomers), or which do not behave as image and mirror image (diastereomers). The invention relates both to the enantiomers and to the racemates, as well as the pure diastereomer and mixtures thereof. The racemates, like the diastereomers, can be separated into the stereoisomerically uniform constituents according to known methods.

Especially preferred are compounds of the general formula (I), wherein $R^1$ denotes 1-naphthyl or 3-halo-phenyl.

Hydrates of the compounds of the invention are stoichiometric compositions of the compounds with water, such as for example hemi-, mono-, or dihydrates.

Solvates of the compounds of the invention or their salts are stoichiometric compositions of the compounds with solvents.

$(C_1-C_8)$-alkyl, and $(C_1-C_4)$-alkyl in general represent straight chain or branched alkyl residues with 1 to 8, or 1 to 4 carbon atoms, respectively. The alkyl residues can be saturated or partially unsaturated, i.e. contain one or more double and/or triple bonds. Saturated alkyl residues are preferred. The following alkyl residues are mentioned by way of example: methyl, ethyl, n-propyl, isopropyl, allyl, propargyl, tert.butyl, pentyl, hexyl, heptyl, and octyl, ($C_6$–$C_{10}$)-Aryl in general represents an aromatic residue with 6 to 10 carbon atoms. Phenyl and naphthyl are preferred.

3- to 10-membered carbocyclyl in general represents a mono- or polycyclic, carbocyclic residue with 3 to 10 ring atoms. 3- to 8-membered carbocyclyl is preferred. Mono- and bicyclic carbocyclyl residues are preferred. Especially preferred are monocyclic carbocyclyl residues. The carbocyclyl residues can be saturated or partially unsaturated. Saturated carbocyclyl residues are preferred. Especially preferred are ($C_3$–$C_{10}$)-cycloalkyl and ($C_4$–$C_7$)-cycloalkyl residues. The following carbocyclyl residues are mentioned by way of example: cyclopropyl, cyclobutyl, cyclopentyl, cyclopentenyl, cyclohexyl, cycloheptyl, norborn-1-yl, norborn-2-yl, norborn-7-yl, norborn-2-en-7-yl, cyclooctyl, cubyl, cyclononyl, cyclodecyl, decalinyl, adamant-1-yl, adamant-2-yl.

Halogen in general represents fluoro, chloro, bromo and iodo. Fluoro, chloro, and bromo are preferred. Fluoro, and chloro are especially preferred.

Unless specified otherwise, when groups in compounds of the invention are optionally substituted, substitution by up to three identical or different residues is generally preferred.

The invention furthermore provides a process for preparing the compounds of the general formula (I) according to the invention, characterized in that compounds of the general formula (II)

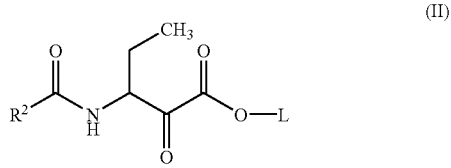

(II)

in which $R^2$ is as defined above and

L represents straight-chain or branched alkyl having up to 4 carbon atoms, are condensed with compounds of the general formula (III)

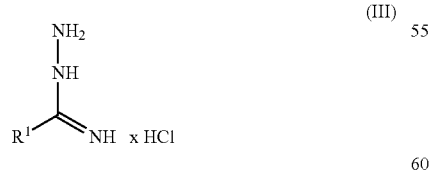

(III)

in which $R^1$ is as defined above, preferably using ethanol as a solvent, to the compounds of the general formula (IV),

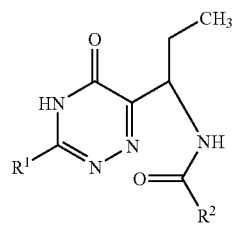

(IV)

in which $R^1$ and $R^2$ are as defined above, which can optionally after isolation be reacted with a dehydrating agent, preferably phosphorus oxytrichloride, to yield the compounds of the general formula (I).

The compounds of the general formula (IV) can alternatively be prepared by

[A] condensation of compounds of the general formula (IIa),

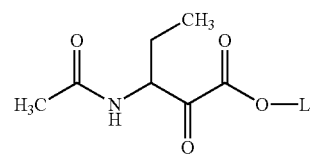

(IIa)

in which

L is as defined above, with compounds of the general formula (III) to compounds of the general formula (IVa),

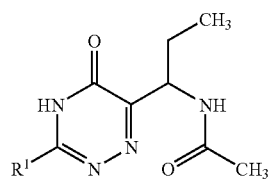

(IVa)

in which $R^1$ is as defined above, preferably using ethanol as a solvent,

[B] followed by hydrolysis of the compounds of the general formula (IVa) to compounds of the general formula (V),

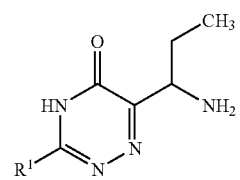

(V)

in which $R^1$ is as defined above,

[C] and finally by condensation of the compounds of the general formula (V) with compounds of the general formula (VI), 5
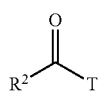
(VI)
6
in which
R² is as defined above, and
T represents a leaving group, preferably chlorine.
The process according to the invention can be illustrated using the following scheme as an example:
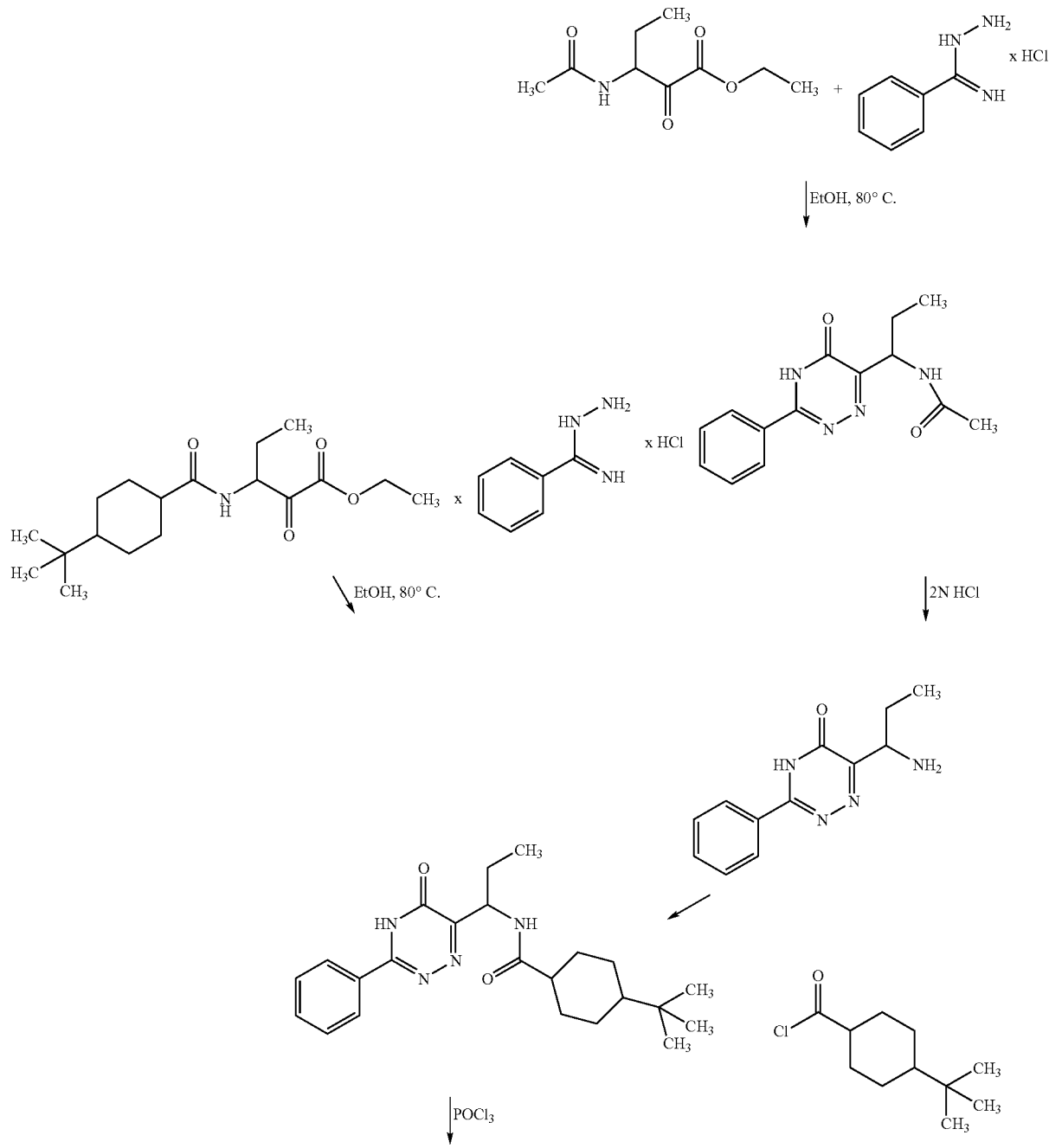

-continued

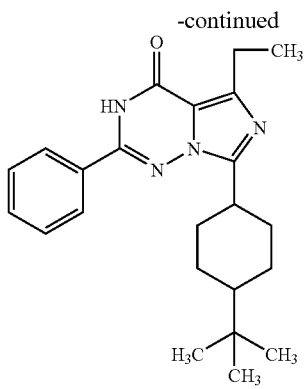

Solvents which are suitable for the individual steps are the customary organic solvents which do not change under the reaction conditions. These preferably include ethers, such as diethyl ether, dioxane, tetrahydrofuran, glycol dimethyl ether, or hydrocarbons, such as benzene, toluene, xylene, hexane, cyclohexane or mineral oil fractions, or halogenated hydrocarbons, such as dichloromethane, trichloromethane, carbon tetrachloride, dichloroethane, trichloroethylene or chlorobenzene, or ethyl acetate, dimethylformamide, hexamethylphosphoric triamide, acetonitrile, acetone, dimethoxyethane or pyridine. It is also possible to use mixtures of the above-mentioned solvents. Particular preference is given to ethanol for the reaction II/IIa+III→IV/IVa and dichloroethane for the cyclisation IV→I.

The reaction temperature can generally be varied within a relatively wide range. In general, the reaction is carried out in a range of from −20° C. to 200° C., preferably of from 0° C. to 100° C.

The process steps according to the invention are generally carried out under atmospheric pressure. However, it is also possible to operate under superatmospheric pressure or under reduced pressure (for example, in a range of from 0.5 to 5 bar).

The compounds of the general formula (IVa) are preferably hydrolysed to compounds of the general formula (V) under acidic conditions as for example in refluxing 2N hydrochloric acid.

The compounds of the general formula (V) are condensed with the compounds of the general formula (VI) to compounds of the general formula (IV) in inert solvents, if appropriate in the presence of a base.

Suitable inert solvents are the customary organic solvents which do not change under the reaction conditions. These preferably include ethers, such as diethyl ether, dioxane, tetrahydrofuran, glycol dimethyl ether, or hydrocarbons, such as benzene, toluene, xylene, hexane, cyclohexane or mineral oil fractions, or halogenated hydrocarbons, such as dichloromethane, trichloromethane, carbon tetrachloride, dichloroethylene, trichloroethylene or chlorobenzene, or ethyl acetate, dimethylformamide, hexamethylphosphoric triamide, acetonitrile, acetone, dimethoxyethane or pyridine. It is also possible to use mixtures of the abovementioned solvents.

Suitable bases are generally alkali metal hydrides or alkali metal alkoxides, such as, for example, sodium hydride or potassium tert-butoxide, or cyclic amines, such as, for example, piperidine, pyridine, dimethylaminopyridine or ($C_1$–$C_4$)-alkylamines, such as, for example, triethylamine. Preference is given to triethylamine, pyridine and/or dimethylaminopyridine.

The base is generally employed in an amount of from 1 mol to 4 mol, preferably from 1.2 mol to 3 mol, in each case based on 1 mol of the compound of the formula (V).

The reaction temperature can generally be varied within a relatively wide range. In general, the reaction is carried out in a range of from −20° C. to 200° C., preferably of from 0° C. to 100° C.

Some of the compounds of the general formula (II) are known, or they are novel, and they can then be prepared by converting compounds of the general formula (VI)

$$R^2\text{—CO-T} \qquad \text{(VI)}$$

in which
$R^2$ is as defined above and
T represents halogen, preferably chlorine,
initially by reaction with α-amino-butyric acid in inert solvents, if appropriate in the presence of a base and trimethylsilyl chloride, into the compounds of the general formula (VII),

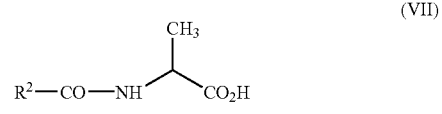

(VII)

in which
$R^2$ is as defined above,
and finally reacting with the compound of the formula (VIII)

(VIII)

in which
L is as defined above,
in inert solvents, if appropriate in the presence of a base.

The compounds of the general formula (IIa) can be prepared analogously.

Suitable solvents for the individual steps of the process are the customary organic solvents which do not change under the reaction conditions. These preferably include ethers, such as diethyl ether, dioxane, tetrahydrofuran, glycol dimethyl ether, or hydrocarbons, such as benzene, toluene, xylene, hexane, cyclohexane or mineral oil fractions, or halogenated hydrocarbons, such as dichloromethane, trichloromethane, carbon tetrachloride, dichloroethylene, trichloroethylene or chlorobenzene, or ethyl acetate, dimethylformamide, hexamethylphosphoric triamide, acetonitrile, acetone, dimethoxyethane or pyridine. It is also possible to use mixtures of the above-mentioned solvents. Particular preference is given to dichloromethane for the first step and to a mixture of tetrahydrofuran and pyridine for the second step.

Suitable bases are generally alkali metal hydrides or alkali metal alkoxides, such as, for example, sodium hydride or potassium tert-butoxide, or cyclic amines, such as, for example, piperidine, pyridine, dimethylaminopyridine or $(C_1-C_4)$-alkylamines, such as, for example, triethylamine. Preference is given to triethylamine, pyridine and/or dimethylaminopyridine.

The base is generally employed in an amount of from 1 mol to 4 mol, preferably from 1.2 mol to 3 mol, in each case based on 1 mol of the compound of the formula (V).

The reaction temperature can generally be varied within a relatively wide range. In general, the reaction is carried out in a range of from −20° C. to 200° C., preferably of from 0° C. to 100° C.

The compounds of the general formulae (VI) and (VIII) are known per se, or they can be prepared by customary methods.

The compounds of the general formula (III) are known or can be prepared by reacting compounds of the general formula (IX)

$$R^1\text{—}Y \quad (IX)$$

in which
$R^1$ is as defined above, and
Y represents a cyano, carboxyl, methoxycarbonyl or ethoxycarbonyl group,
with ammonium chloride in toluene and in the presence of trimethylaluminium in hexane in a temperature range of from −20° C. to room temperature, preferably at 0° C. and atmospheric pressure, and reacting the resulting amidine, if appropriate in situ, with hydrazine hydrate.

The compounds of the general formula (IX) are known per se, or they can be prepared by customary methods.

The compounds of the general formula (I) inhibit the PDE 4 resident in the membranes of human neutrophils and display an especially favourable binding profile versus the PDE 4 high affinity site, binding to which is made responsible for side effects like emesis. One measured functional consequence of this inhibition was inhibition of superoxide anion production by stimulated human neutrophils.

The compounds of the general formula (I) can therefore be employed in medicaments for the treatment of inflammatory processes, esp. acute and chronic inflammatory processes, and/or immune diseases.

The compounds according to the invention are preferably suitable for the treatment and prevention of inflammatory processes, i.e. acute and chronic inflammatory processes, and/or immune diseases, such as emphysema, alveolitis, shock lung, all kinds of chronic obstructive pulmonary diseases (COPD), adult respiratory distress syndrome (ARDS), asthma, bronchitis, cystic fibrosis, eosinophilic granuloma, arteriosclerosis, arthrosis, inflammation of the gastro-intestinal tract, myocarditis, bone resorption diseases, reperfusion injury, Crohn's disease, ulcerative colitis, systemic lupus erythematosus, type I diabetes mellitus, psoriasis, anaphylactoid purpura nephritis, chronic glomerulonephritis, inflammatory bowel disease, atopic dermatitis, other benign and malignant proliferative skin diseases, allergic rhinitis, allergic conjunctivitis, vernal conjunctivitis, arterial restenosis, sepsis and septic shock, toxic shock syndrome, grafts vs. host reaction, allograft rejection, treatment of cytokine-mediated chronic tissue degeneration, rheumatoid arthritis, arthritis, rheumatoid spondylitis, osteoarthritis, coronary insufficiency, myalgias, multiple sclerosis, malaria, AIDS, cachexia, prevention of tumor growth and tissue invasion, leukemia, depression, memory impairment and acute stroke. The compounds according to the invention are additionally suitable for reducing the damage to infarct tissue after reoxygenation.

The compounds of formula (I) according to the invention can be used as active compound components for the production of medicaments. For this, they can be converted into the customary formulations such as tablets, coated tablets, aerosols, pills, granules, syrups, emulsions, suspensions and solutions in a known manner using inert, non-toxic, pharmaceutically suitable excipients or solvents. Preferably, the compounds according to the invention are used here in an amount such that their concentration in the total mixture is approximately 0.5 to approximately 90% by weight, the concentration, inter alia, being dependent on the corresponding indication of the medicament.

The above-mentioned formulations are produced, for example, by extending the active compounds with solvents and/or excipients having the above properties, where, if appropriate, additionally emulsifiers or dispersants and, in the case of water as the solvent, alternatively an organic solvent, have to be added.

Administration is carried out in a customary manner, preferably orally, transdermally or parenterally, for example perlingually, buccally, intravenously, nasally, rectally or inhalationally.

For human use, in the case of oral administration, it is recommendable to administer doses of from 0.001 to 50 mg/kg, preferably of 0.01 mg/kg–20 mg/kg. In the case of parenteral administration, such as, for example, intravenously or via mucous membranes nasally, buccally or inhalationally, it is recommendable to use doses of 0.001 mg/kg–0.5 mg/kg.

In spite of this, if appropriate, it may be necessary to depart from the amounts mentioned above, namely depending on the body weight or the type of administration route, on the individual response towards the medicament, the manner of its formulation and the time or interval at which administration takes place. Thus, in some cases it may be sufficient to manage with less than the above mentioned minimum amount, while in other cases the upper limit mentioned must be exceeded. In the case of the administration of relatively large amounts, it may be recommendable to divide these into several individual doses over the course of the day.

Test Descriptions
1. Preparation of human PMN
   Human PMN (polymorphonuclear neutrophil leucocytes) are readily purified from peripheral blood. Phosphodiesterase in these cells is predominantly located in the membrane fraction. Inhibitory potency of compounds against this preparation correlate well with the anti-inflammatory activity as measured by inhibiton of superoxide production.
   Blood was taken from healthy subjects by venous puncture and neutrophils were purified by dextran sedimentation and density gradient centrifugation on Ficoll Histopaque and resuspended in the buffered medium.
2. Assay of human PMN phosphodiesterase
   This was performed as a particulate fraction from human PMN essentially as described by Souness and Scott [Biochem. J. 291, 389–395 (1993)].
   Particulate fractions were treated with sodium vanadate/ glutathione as described by the authors to express the descrete stereospecific site on the phosphodiesterase enzyme. The prototypical PDE 4 inhibitor, rolipram, had an $IC_{50}$ value in the range 450 nM–1500 nM, thus defining this preparation as the so-called "low affinity" [L] form. The preparation examples had $IC_{50}$ values within the range of 0.11 nM–10,000 nM.

3. Inhibition of FMLP-stimulated production of superoxide radical anions

Neutrophils ($2.5 \times 10^5$ ml$^{-1}$) were mixed with cytochrome C (1.2 mg/ml) in the wells of a microtitre plate. Compounds according to the invention were added in dimethyl sulphoxide (DMSO). Compound concentration ranged from 2.5 nM to 10 µM, the DMSO concentration was 0.1% v/v in all wells. After addition of cytochalasin b (5 µg×ml$^{-1}$) the plate was incubated for 5 min at 37° C. Neutrophils were then stimulated by addition of $4 \times 10^{-8}$ M FMLP (N-Formyl-Met-Leu-Phe) and superoxide generation measured as superoxide dismutase inhibitable reduction of cytochrome C by monitoring the $OD_{550}$ in a Thermomax microtitre plate spectrophotometer. Initial rates were calculated using a Softmax kinetic calculation programme. Blank wells contained 200 units of superoxide dismutase.

The inhibition of superoxide production was calculated as follows:

$$\frac{[1 - (Rx - Rb)]}{(Ro - Rb)} \times 100$$

Rx=Rate of the well containing the compound according to the invention
Ro=Rate in the control well
Rb=Rate in the superoxide dismutase containing blank well The preparation examples had $IC_{50}$ values within the range of 0.1 nM–10,000 nM.

4. Assay of binding to the rolipram binding site (PDE 4 high affinity site; "H-PDE 4 Form") in Rat Brain Membranes The activity of compounds on the PDE 4 high affinity site ("H-PDE 4 form") is readily measured by determining their potency for displacement of [$^3$H]-rolipram from its binding site in rat brain membranes. Activity at this site is believed to be a measure of side effect potential (e.g. stimulation of stomach acid secretion, nausea and emesis).

The rolipram binding site assay was performed essentially as described by Schneider et al. [Eur. J. Pharmacol. 127, 105–115 (1986)].

5. Lipopolysaccharide (LPS)-induced neutrophil influx into rat lung

Intranasal administration of LPS to rats causes a marked influx of neutrophils into the lungs measurable by histological or biochemical (myeloperoxidase content of the cell pellet) analysis of the bronchoalveolar lavage fluid 24 h later. Rats were treated with test compound or vehicle administered by the oral route 1 h prior to and 6 h after administration of intranasal LPS. 24 hours later animals were euthanatized and their lungs lavaged with PBS (phosphate buffered saline). Neutrophil and total cell numbers were analysed.

6. Emetic potential in the marmoset

Vehicle or test compound was administered by the oral route to conscious marmosets. Animals were observed for emetic episodes or abnormal behaviour for 1 h post dosing. In some experiments, if no adverse response was seen, a separate group of animals was tested at ½ log dose higher until emesis or abnormal behaviour was observed. The highest dose at which no abnormal behavior or emetic episodes occurred was recorded as the NOEL.

Materials and Methods

| LC-parameters | solution A acetonitrile |
| | solution B 0.3 g 30% HCl/l water |
| | column oven 50° C.; |
| | column Symmetry C18 2.1 × 150 mm |
| gradient: | time [min]   % A   % B   flow [ml/min] |
| | 0   10   90   0.9 |
| | 3   90   10   1.2 |
| | 6   90   10   1.2 |

| LC-parameters | solution A acetonitrile/0.1% formic acid |
| | solution B water/0.1% formic acid |
| | column oven 40° C.; |
| | column Symmetry C18 2.1 × 50 mm |
| gradient: | time [min]   % A   % B   flow [ml/min] |
| | 0   10   90   0.5 |
| | 4   90   10   0.5 |
| | 6   90   10   0.5 |
| | 6.1   10   90   1.0 |
| | 7.5   10   90   0.5 |

| Column: | HP-5 30 m × 320 µm × 0.25 µm |
| Carrier Gas: | Helium |
| Mode: | Constant flow, initial flow: 1.5 ml/min |
| Oven ramp: | initial temp: 60° C. |
| | initial time: 1 min |
| | rate: 14° C./min up to 300° C., then 300° C. 2 min |

Unless specified otherwise, the following chromatographic conditions were applied: chromatography was performed on silica gel Si 60; for flash chromatography, the usual conditions were followed as described in Still, *J. Org. Chem.* 43, 2923 (1978); mixtures of dichloromethane and methanol or cyclohexane and ethylacetate were used as eluants. Unless specified otherwise, reactions were executed under an argon atmosphere and under anhydrous conditions.

Abbreviations:

| HPLC = | high performance liquid chromatography |
| MS = | mass spectroscopy |
| NMR = | nuclear magnetic resonance spectroscopy |
| LC-MS = | liquid chromatography combined with mass spectroscopy |
| GC-MS = | gas chromatography combined with mass spectroscopy |
| MeOH = | methanol |
| DMF = | N,N-dimethylformamide |
| DMSO = | dimethylsulfoxide |

Starting Materials

EXAMPLE 1A 2-(Acetylamino)butanoic acid

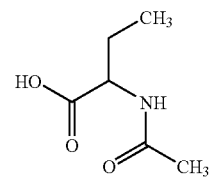

163 g (1.58 mol) 2-aminobutanoic acid are dissolved in acetic acid, and 242 g (2.37 mol) acetic anhydride are added dropwise. The mixture is stirred for 2 h at 100° C. until completion of reaction, then the solution evaporated to dryness in vacuo. The solid residue is suspended in ethyl acetate, filtered and washed with diethyl ether.

Yield: 220 g (96%) ¹H-NMR (Methanol-d₄): δ=0.97 (t, 3 H), 1.65–1.93 (m, 2 H), 1.99 (s, 3 H), 4.29 (q, 1 H) ppm.

EXAMPLE 2A

Ethyl 3-(acetylamino)-2-oxopentanoate

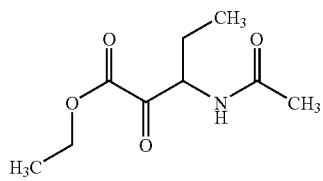

9.2 g (63.4 mmol) 2-(Acetylamino)butanoic acid are suspended in 120 ml tetra-hydrofurane and heated to reflux together with 15.0 g (190 mmol) pyridine and a bit of N,N-dimethylaminopyridine. While heating at reflux, 17.3 g (127 mmol) ethyl chloro(oxo)acetate are added dropwise. The reaction mixture is heated at reflux until no more evolution of gas can be observed. After cooling down to room temperature, the reaction mixture is added to ice water and the organic phase extracted with ethyl acetate. The dried organic phase is evaporated to dryness in vacuo, dissolved in ethanol and the solution directly used for the next reaction.

EXAMPLE 3A

3-Bromobenzenecarboximidamide hydrochloride

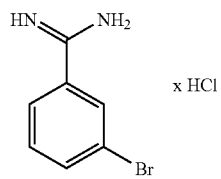

1.18 g (22 mmol, 2 equiv.) ammonium chloride are suspended in 40 ml of dry toluene under an argon atmosphere, and the mixture is cooled to 0° C. 11 ml (22 mmol, 2 equiv.) of a 2M solution of trimethylaluminium in hexane are added dropwise, and the reaction mixture is stirred at room temperature until no more evolution of gas is observed. After addition of 2.0 g (11 mmol, 1 equiv.) 3-bromo-benzonitrile, the mixture is stirred at 80° C. bath temperature over night. It is then cooled down to 0° C. and 50 ml of methanol are added with subsequent stirring of 1 hour at room temperature. After filtration, the solid is washed with methanol for several times, the solution is evaporated to dryness in vacuo and the residue washed with methanol.

Yield: 2.02 g (78%) ¹H-NMR (DMSO-d₆, 300 MHz): δ=7.6 (m, 1H), 7.8 (m, 1H), 8.0 (m, 1H), 8.1 (s, 1H) ppm.

EXAMPLE 4A

4-Fluorobenzenecarboximidamide hydrochloride

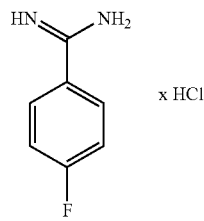

In analogy to the procedure for Example 3A, 2.0 g (16.5 mmol) 4-fluorobenzonitrile and proportionate amounts of the other reagents are used.

Yield: 2.9 g (100%) ¹H-NMR (DMSO-d₆, 200 MHz): δ=7.5 (m, 2H), 8.0 (m, 2H) ppm.

EXAMPLE 5A

Cyclopropanecarboximidamide hydrochloride

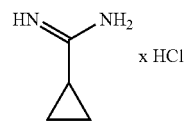

In analogy to the procedure for Example 3A, 6.71 g (100 mmol) cyclopropanecarbonitrile and proportionate amounts of the other reagents are used.

Yield: 7.3 g (61%) GC/MS (method A): retention time 3.42 min., m/z 85.1 [M+H]⁺

EXAMPLE 6A

Cyclopentanecarboximidamide hydrochloride

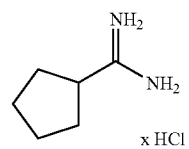

In analogy to the procedure for Example 3A, 7.51 g (79.0 mmol) cyclopentanecarbonitrile and proportionate amounts of the other reagents are used.

Yield: 3.9 g (33%) LC-MS (method A): retention time 0.42 min., m/z 113 [M+H]⁺

EXAMPLE 7A 2,2-Dimethylpropaneimidamide hydrochloride

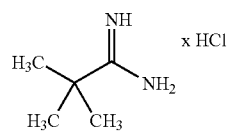

In analogy to the procedure for Example 3A, 8.31 g (100 mmol) pivalonitrile and proportionate amounts of the other reagents are used. The crude product is used in the next step without further purification.

Yield: 6 g crude product

EXAMPLE 8A

3-Nitrobenzenecarboximidamide hydrochloride

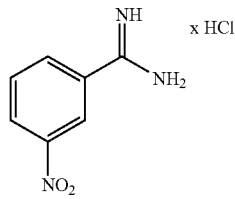

In analogy to the procedure for Example 3A, 30.0 g (203 mmol) 3-nitrobenzonitrile and proportionate amounts of the other reagents are used.

Yield: 24.5 g (47%) LC-MS (method A): retention time 0.40 min., m/z 166 [M+H]$^+$

EXAMPLE 9A

1-Naphthalenecarboximidamide hydrochloride

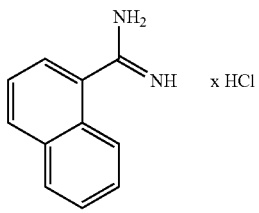

14 g (261 mmol, 2 equiv.) ammonium chloride are suspended in 150 ml of dry toluene under an argon atmosphere, and the mixture is cooled to 0° C. 130 ml (260 mmol, 2 equiv.) of a 2M solution of trimethylaluminium in hexane are added dropwise, and the reaction mixture is stirred at room temperature until no more evolution of gas is observed. After addition of 20 g (130 mmol, 1 equiv.) 1-cyano-naphthalene, the mixture is stirred at 80° C. bath temperature over night. The mixture is cooled and poured into a slurry of silica in methylene chloride. After filtration, the solid is washed with methanol for several times, the solution is evaporated to dryness in vacuo and the residue washed with methanol. The combined filtrates are pooled and stirred in a mixture of methylene chloride containing 10% methanol.

Yield: 9.88 g (37%) $^1$H-NMR (DMSO-d$_6$, 300 MHz): δ=7.6–7.8 (m, 4H), 8.0 (d, 1H), 8.1 (m, 1H), 8.2 (d, 1H) ppm; 9.5 (br s, 4H) ppm.

EXAMPLE 10A

N-{1-[3-(3-Bromophenyl)-5-oxo-4,5-dihydro-1,2,4-triazin-6-yl]propyl}acetamide

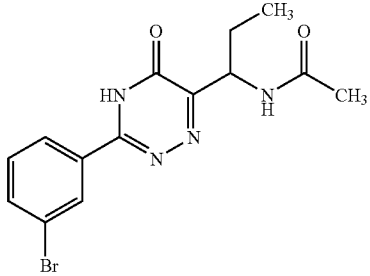

2.02 (8.6 mmol, 1 equiv.) 3-bromobenzenecarboximidamide hydrochloride are suspended in 50 ml of ethanol and 1.47 g (10.2 mmol, 1.2 equiv.) hydrazine hydrate are added. After stirring at room temperature for 1 hour, 2.59 g (13 mmol, 1.5 equiv) of the compound of Example 2A, dissolved in 10 ml of ethanol, are added. The reaction mixture is stirred at 80° C. (bath temperature) for 4 hours and then at room temperature over night. The mixture is evaporated to dryness in vacuo and the product is purified by chromatography (flash or column chromatography or preparative HPLC).

Yield: 758 mg (25%) $^1$H-NMR (DMSO-d$_6$, 200 MHz): δ=0.9 (t, 3H), 1.6 (m, 1H), 1.8 (m, 1H), 1.9 (s, 3H), 4.9 (m, 1H), 7.5 (m, 1H), 7.8 (m, 1H), 8.0 (m, 1H), 8.2 (m, 2H), 14.1 (br. s, 1H) ppm.

EXAMPLE 11A

N-{1-[3-(4-Fluorophenyl)-5-oxo-4,5-dihydro-1,2,4-triazin-6-yl]propyl}acetamide

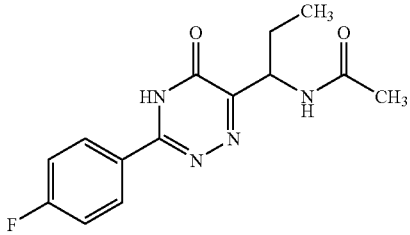

In analogy to the procedure for Example 10A, 2.0 g (11.4 mmol) 4-fluorobenzenecarboximidamide hydrochloride and proportionate amounts of the other reagents are used.

Yield: 1.47 g (44%) $^1$H-NMR (DMSO-d$_6$, 300 MHz): δ=0.9 (t, 3H), 1.6 (m, 1H), 1.8 (m, 1H), 1.9 (s, 3H), 4.9 (m, 1H), 7.5 (m, 2H), 8.1 (m, 3H), 14.1 (br. s, 1H) ppm.

EXAMPLE 12A

N-{1-[3-(3-Fluorophenyl)-5-oxo-4,5-dihydro-1,2,4-triazin-6-yl]propyl}acetamide

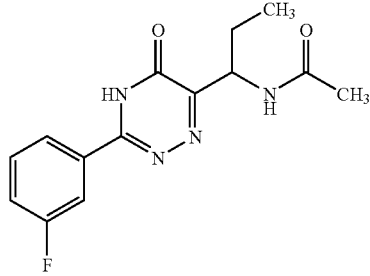

In analogy to the procedure for Example 10A, 2.0 g (11.4 mmol) 3-fluorobenzenecarboximidamide hydrochloride and proportionate amounts of the other reagents are used.

Yield: 781 mg (23%) $^1$H-NMR (DMSO-$d_6$, 300 MHz): δ=0.9 (t, 3H), 1.6 (m, 1H), 1.8 (m, 1H), 1.9 (s, 3H), 4.9 (m, 1H), 7.5 (m, 1H), 7.7 (m, 1H), 7.8 (m, 1H), 7.9 (m, 1H), 8.2 (d, 1H), 14.1 (br. s, 1H) ppm.

EXAMPLE 13A

N-{1-[3-(3-Chlorophenyl)-5-oxo-4,5-dihydro-1,2,4-triazin-6-yl]propyl}acetamide

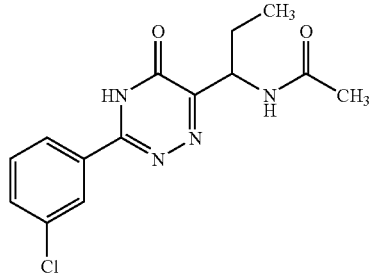

In analogy to the procedure for Example 10A, 1.5 g (7.9 mmol) 3-chlorobenzenecarboximidamide hydrochloride and proportionate amounts of the other reagents are used.

Yield: 441 mg (18%) $^1$H-NMR (DMSO-$d_6$, 300 MHz): δ=0.9 (t, 3H), 1.6 (m, 1H), 1.8 (m, 1H), 1.9 (s, 3H), 4.9 (m, 1H), 7.6 (m, 1H), 7.7 (m, 1H), 8.0 (m, 1H), 8.1 (m, 1H), 8.2 (d, 1H), 14.1 (br. s, 1H) ppm.

EXAMPLE 14A

N-{1-[3-(2-Bromophenyl)-5-oxo-4,5-dihydro-1,2,4-triazin-6-yl]propyl}acetamide

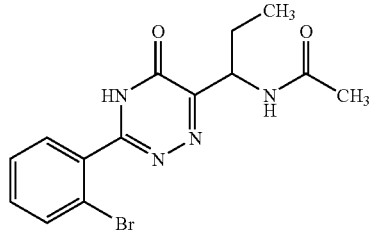

In analogy to the procedure for Example 10A, 1.64 g (7.0 mmol) 2-bromobenzenecarboximidamide hydrochloride and proportionate amounts of the other reagents are used.

Yield: 1.0 g (41%) LC/MS (B): MS (ES+): 351 (M+H$^+$), retention time 2.34 min.

EXAMPLE 15A

N-[1-(3-Cyclohexyl-5-oxo-4,5-dihydro-1,2,4-triazin-6-yl)propyl]acetamide

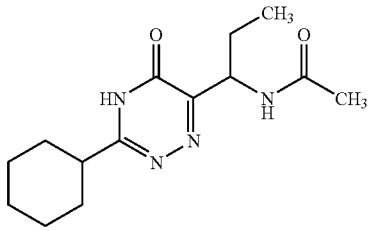

In analogy to the procedure for Example 10A, 1.50 g (9.2 mmol) cyclohexanecarboximidamide hydrochloride and proportionate amounts of the other reagents are used.

Yield: 1.17 g (46%) $^1$H-NMR (DMSO-$d_6$, 200 MHz): δ=0.9 (t, 3H), 1.2 (m, 3H), 1.5 (m, 3H), 1.8 (m, 4H), 1.9 (s, 3H), 2.5 (m, 1H), 4.8 (m, 1H), 8.1 (d, 1H), 13.4 (br.s, 1H) ppm.

EXAMPLE 16A

N-{1-[3-(4-Bromophenyl)-5-oxo-4,5-dihydro-1,2,4-triazin-6-yl]propyl}acetamide

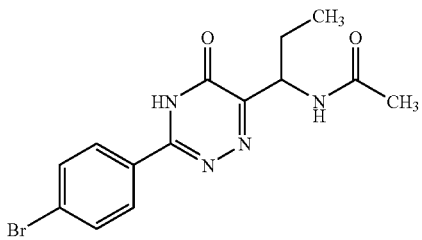

In analogy to the procedure for Example 10A, 10.2 g (43.3 mmol) 4-bromobenzenecarboximidamide hydrochloride and proportionate amounts of the other reagents are used.

Yield: 5.23 g (34%) $^1$H-NMR (400 MHz, CD$_3$OD): δ=1.01 (t, 3 H), 1.66–1.79 (m, 1 H), 1.91–2.06 (m, 4 H, s at 1.99), 5.02–5.09 (m, 1 H), 7.75 (d, 2 H), 7.93 (d, 2 H) ppm.

EXAMPLE 17A

N-[1-(3-Cyclopropyl-5-oxo-4,5-dihydro-1,2,4-triazin-6-yl)propyl]acetamide

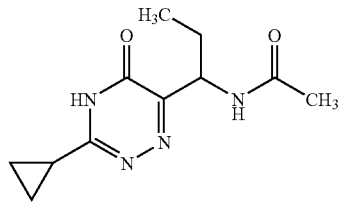

In analogy to the procedure for Example 10A, 7.30 g (60.5 mmol) cyclopropanecarboximidamide hydrochloride and proportionate amounts of the other reagents are used. The crude product is used in the next step without further purification.

Yield: 4.9 g (34%) crude material

EXAMPLE 18A

N-[1-(3-Cyclopentyl-5-oxo-4,5-dihydro-1,2,4-triazin-6-yl)propyl]acetamide

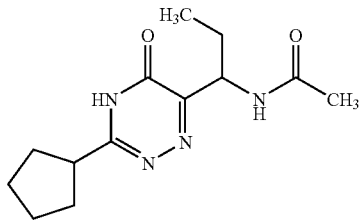

In analogy to the procedure for Example 10A, 3.50 g (23.6 mmol) cyclopentanecarboximidamide hydrochloride and proportionate amounts of the other reagents are used.

Yield: 1.7 g (27%) LC/MS (method A): retention time 1.60 min., m/z 265 [M+H]$^+$

EXAMPLE 19A

N-[1-(3-tert-Butyl-5-oxo-4,5-dihydro-1,2,4-triazin-6-yl)propyl]acetamide

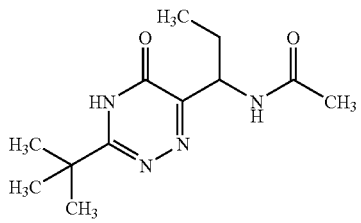

In analogy to the procedure for Example 10A, 6.0 g (11.0 mmol) 2,2-dimethylpropaneimidamide hydrochloride and proportionate amounts of the other reagents are used.

Yield: 1.77 g (64%) LC/MS (method A): retention time 1.59 min., m/z 253 [M+H]$^+$

EXAMPLE 20A

N-{1-[3-(3-Nitrophenyl)-5-oxo-4,5-dihydro-1,2,4-triazin-6-yl]propyl}acetamide

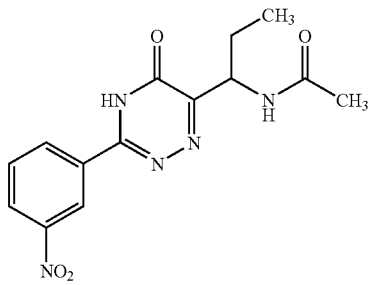

In analogy to the procedure for Example 10A, 35.0 g (174 mmol) 3-nitrobenzenecarboximidamide hydrochloride and proportionate amounts of the other reagents are used.

Yield: 13.6 g (25%) $^1$H-NMR (200 MHz, CDCl$_3$): δ=0.97 (t, 3 H), 1.83–2.08 (m, 5 H, s at 2.02), 5.09 (m, 1 H), 7.76 (t, 1 H), 8.45 (d, 1H), 8.58 (d, 1H), 9.12 (s, 1 H) ppm.

EXAMPLE 21A

N-[1-(5-Oxo-3-phenyl-4,5-dihydro-1,2,4-triazin-6-yl)propyl]acetamide

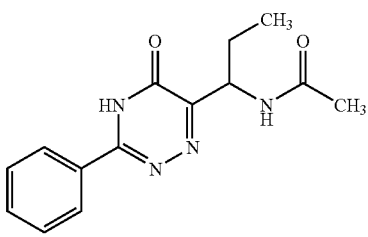

In analogy to the procedure for Example 10A, 7.26 g (46.8 mmol) benzenecarboximidamide hydrochloride and proportionate amounts of the other reagents are used.

Yield: 10.1 g (80%) $^1$H-NMR (DMSO-d$_6$, 300 MHz): δ=0.9 (t, 3H), 1.5 (m, 1H), 1.8 (m, 1H), 1.9 (s, 3H), 4.9 (m, 1H), 7.5 (m, 3H), 8.1 (m, 3H), 14.1 (br. s, 1H) ppm.

EXAMPLE 22A

N-{1-[3-(1-Naphthyl)-5-oxo-4,5-dihydro-1,2,4-triazin-6-yl]propyl}acetamide

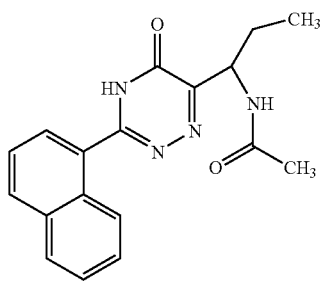

1.0 g (4.84 mmol, 1 equiv.) 1-Naphthalenecarboximidamide hydrochloride are suspended in 2 ml of DMSO and 0.29 g (5.81 mmol, 1.2 equiv.) hydrazine hydrate are added. After stirring at room temperature for 16 hours, 1.45 g (7.3 mmol, 1.5 equiv.) of the compound of Example 2A, dissolved in 10 ml of ethanol, are added. The reaction mixture is stirred at reflux for 1 hour and then at 60° C. (bath temperature) for 4 hours and then at room temperature over night. The mixture is evaporated to dryness in vacuo and the product is purified by flash chromatography.

Yield: 7.1 g (70%) $^1$H-NMR (DMSO-d$_6$, 300 MHz): δ=1.0 (t, 3H), 1.6–1.7 (m, 2H), 1.9 (s, 3H), 5.0 (m, 1H), 7.5–8.2 (m, 8H), 14.0 (br. s, 1H) ppm.

EXAMPLE 23A 6-(1-Aminopropyl)-3-(3-bromophenyl)-1,2,4-triazin-5(4H)-one

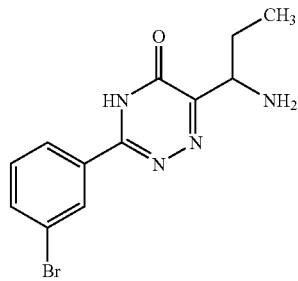

749 mg (2.13 mmol) of Example 10A are heated to reflux in 20 ml 2 N hydrochloric acid for 18 hours. After cooling down to room temperature, the mixture is neutralized with 10% NaOH and, after addition of ethanol, evaporated to dryness in vacuo. The residue is treated with methanol and the filtrate separated from the salts. The filtrate is evaporated to dryness in vacuo and the product purified by chromatography (flash or column chromatography or preparative HPLC).

Yield: 320 mg (49%) $^1$H-NMR (DMSO-$d_6$, 200 MHz): δ=0.9 (t, 3H), 1.9 (m, 2H), 4.3 (d/d, 1H), 7.4 (m, 1H), 7.6 (m, 1H), 8.1 (br. s, 2H), 8.2 (m, 1H), 8.4 (m, 1H) ppm.

EXAMPLE 24A 6-(1-Aminopropyl)-3-(4-fluorophenyl)-1,2,4-triazin-5(4H)-one

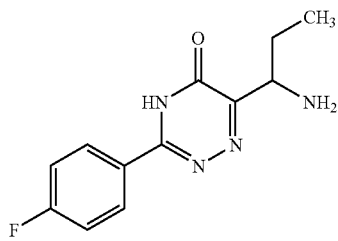

In analogy to the procedure for Example 23A, 1.46 g (5.0 mmol) of Example 11A and proportionate amounts of the other reagents are used.

Yield: 970 mg (78%) LC/MS (A): MS (ESI): 249 (M+H$^+$), retention time 0.50 min

EXAMPLE 25A 6-(1-Aminopropyl)-3-(3-fluorophenyl)-1,2,4-triazin-5(4H)-one

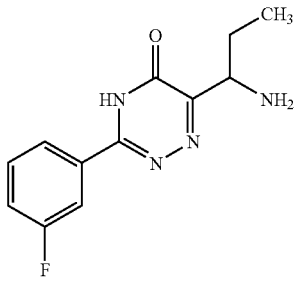

In analogy to the procedure for Example 23A, 1.1 g (3.8 mmol) of Example 12A and proportionate amounts of the other reagents are used.

Yield: 594 mg (63%) LC/MS (A): MS (ESI): 249 (M+H$^+$), retention time 0.49 min

EXAMPLE 26A 6-(1-Aminopropyl)-3-(3-chlorophenyl)-1,2,4-triazin-5(4H)-one

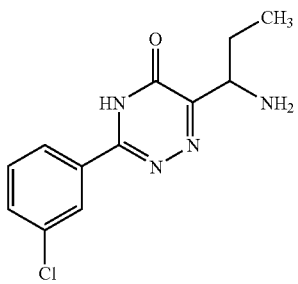

In analogy to the procedure for Example 23A, 419 mg (1.4 mmol) of Example 13A and proportionate amounts of the other reagents are used.

Yield: 280 mg (77%) $^1$H-NMR (DMSO-$d_6$, 300 MHz): δ=0.9 (t, 3H), 1.9 (m, 1H), 2.0 (m, 1H), 4.3 (d/d, 1H), 7.5 (m, 2H), 8.2 (br. m, 4H) ppm.

EXAMPLE 27A 6-(1'-Aminopropyl)-3-(2-bromophenyl)-1,2,4-triazin-5(4H)-one

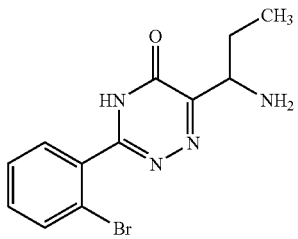

In analogy to the procedure for Example 23A, 1.00 g (2.85 mmol) of Example 14A and proportionate amounts of the other reagents are used.

Yield: 152 mg (17%) $^1$H-NMR (DMSO-$d_6$, 300 MHz): δ=0.9 (t, 3H), 1.9 (m, 1H), 2.0 (m, 1H), 4.3 (d/d, 1H), 7.3 (m, 1H), 7.4 (m, 1H), 7.5 (m, 1H), 7.7 (m, 1H) ppm.

EXAMPLE 28A 6-(1-Aminopropyl)-3-cyclohexyl-1,2,4-triazin-5(4H)-one

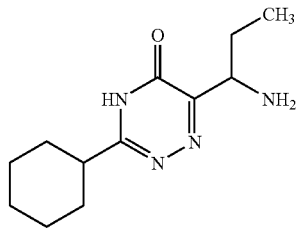

In analogy to the procedure for Example 23A, 1.14 g (4.10 mmol) of Example 15A and proportionate amounts of the other reagents are used.

Yield: 128 mg (13%) $^1$H-NMR (DMSO-$d_6$, 300 MHz): δ=0.9 (t, 3H), 1.3 (m, 3H), 1.5 (m, 2H), 1.7 (m, 1H), 1.8 (m, 4H), 2.6 (m, 1H), 4.3 (m, 1H) ppm.

EXAMPLE 29A 6-(1-Aminopropyl)-3-(4-bromophenyl)-1,2,4-triazin-5(4H)-one

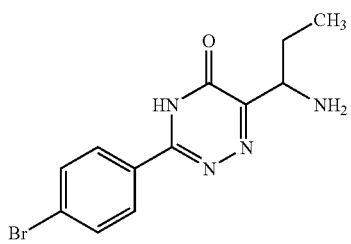

In analogy to the procedure for Example 23A, 5.0 g (14.2 mmol) N-{1-[3-(4-bromophenyl)-5-oxo-4,5-dihydro-1,2,4-triazin-6-yl]propyl}acetamide and proportionate amounts of the other reagents are used.

Yield: 3.4 g (77%) $^1$H-NMR (300 MHz, CD$_3$OD): δ=1.02 (t, 3 H), 1.87–2.22 (m, 5 H, s at 1.96); 4.42–4.53 (t, 1 H), 7.63 (d, 2 H), 8.09 (d, 2 H) ppm.

EXAMPLE 30A 6-(1-Aminopropyl)-3-cyclopropyl-1,2,4-triazin-5(4H)-one

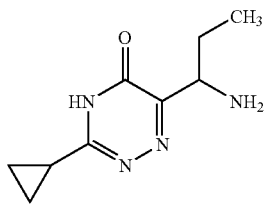

In analogy to the procedure for Example 23A, 4.90 g (20.7 mmol) N-[1-(3-cyclopropyl-5-oxo-4,5-dihydro-1,2,4-triazin-6-yl)propyl]acetamide and proportionate amounts of the other reagents are used.

Yield: 1.6 g (40%) LC/MS (method A): retention time 0.36 min., m/z 195 [M+H]$^+$

EXAMPLE 31A 6-(1-Aminopropyl)-3-tert-butyl-1,2,4-triazin-5(4H)-one

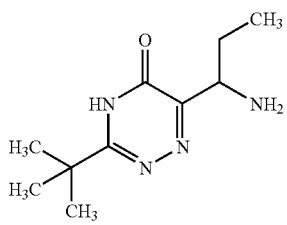

In analogy to the procedure for Example 23A, 1.77 g (4.42 mmol) N-[1-(3-tert-butyl-5-oxo-4,5-dihydro-1,2,4-triazin-6-yl)propyl]acetamide and proportionate amounts of the other reagents are used.

Yield: 850 mg (91%) $^1$H-NMR (400 MHz, CD$_3$OD): δ=0.99 (t, 3H), 1.34 (s, 9H), 1.82–2.12 (m, 2H), 4.34 (t, 1H) ppm.

EXAMPLE 32A 6-(1-Aminopropyl)-3-cyclopentyl-1,2,4-triazin-5(4H)-one

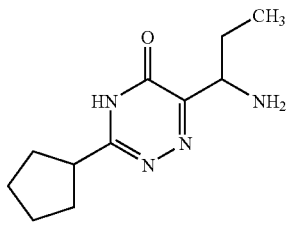

In analogy to the procedure for Example 23A, 1.65 g (6.24 mmol) N-[1-(3-cyclopentyl-5-oxo-4,5-dihydro-1,2,4-triazin-6-yl)propyl]acetamide and proportionate amounts of the other reagents are used.

Yield: 900 mg (65%) $^1$H-NMR (300 MHz, CD$_3$OD): δ=0.99 (t, 3H), 1.64–2.11 (m, 10H), 3.03 (quin., 1H), 4.30 (t, 1H) ppm.

EXAMPLE 33A 6-(1-Aminopropyl)-3-(3-nitrophenyl)-1,2,4-triazin-5(4H)-one

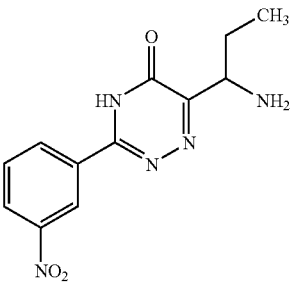

In analogy to the procedure for Example 23A, 13.5 g (42.5 mmol) N-{1-[3-(3-nitrophenyl)-5-oxo-4,5-dihydro-1,2,4-triazin-6-yl]propyl}acetamide and proportionate amounts of the other reagents are used.

Yield: 6.2 g (41%) LC/MS (method A): retention time 0.497 min., m/z 276 [M+H]+

EXAMPLE 34A 6-(1-Aminopropyl)-3-phenyl-1,2,4-triazin-5(4H)-one

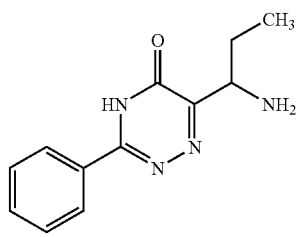

In analogy to the procedure for Example 23A, 10.00 g (36.7 mmol) of Example 21A and proportionate amounts of the other reagents are used.

Yield: 6.7 g (77%) $^1$H-NMR (DMSO-$d_6$, 200 MHz): δ=0.9 (t, 3H), 1.9 (m, 2H), 4.1 (m, 1H), 4.3 (dd, 1H), 7.4 (m, 3H), 8.2 (m, 2H), 8.3 (bs, 2H) ppm.

EXAMPLE 35A 6-(1-Aminopropyl)-3-(1-naphthyl)-1,2,4-triazin-5(4H)-one

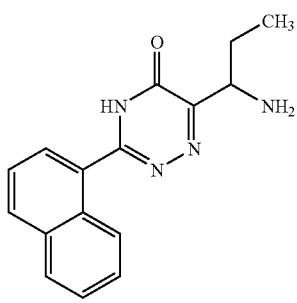

In analogy to the procedure for Example 23A, 700 mg (2.17 mmol) of Example 22A and proportionate amounts of the other reagents are used.

Yield: 557 mg (91%) $^1$H-NMR (DMSO-$d_6$, 300 MHz): δ=0.9 (t, 3H), 1.8–2.2 (m, 2H), 4.4 (d/d, 1H), 7.4–8.7 (m, 10H) ppm.

EXAMPLE 36A

N-{1-[3-(3-Bromophenyl)-5-oxo-4,5-dihydro-1,2,4-triazin-6-yl]propyl}-4-tert-butylcyclohexanecarboxamide

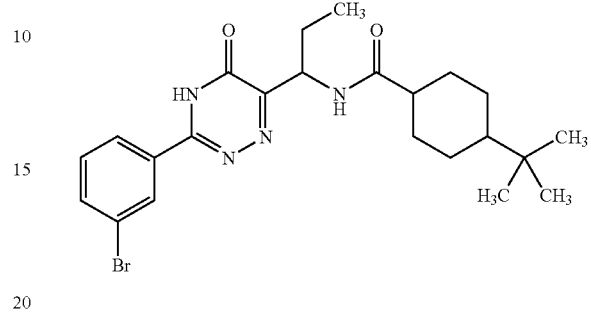

500 mg (1.62 mmol, 1 equiv.) of Example 23A are suspended in 40 ml dichloromethane, 0.48 ml (3.44 mmol, 2 equiv.) triethylamine and 328 mg (1.62 mmol) 4-tert-butylcyclohexanecarbonyl chloride are added. The reaction mixture is stirred at room temperature until completion of reaction (1–2 hours). The reaction mixture is added to the same volume of 1N hydrochloric acid, the organic phase is washed with 1N hydrochloric acid and brine, dried over sodium sulfate and evaporated to dryness. The product is used without further purification or purified by chromatography (flash or column chromatography or preparative HPLC).

LC/MS (A): MS (ESI): 475, 477 (M+H+), retention time 3.17, 3.20 min.

EXAMPLE 37A 4-tert-Butyl-N-[1-(3-cyclopropyl-5-oxo-4,5-dihydro-1,2,4-triazin-6-yl)propyl]-cyclohexanecarboxamide

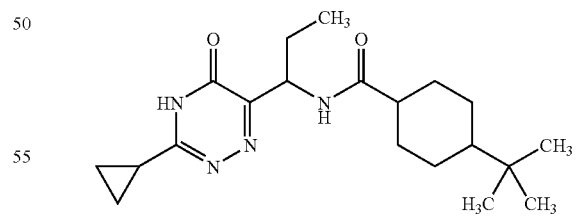

In analogy to the procedure for Example 36A, 250 mg (1.29 mmol) 6-(1-aminopropyl)-3-cyclopropyl-1,2,4-triazin-5(4H)-one, 260 mg (1.29 mmol) 4-tert-butyl-cyclohexanecarbonyl chloride and proportionate amounts of the other reagents are used. The crude product is used in the next step without further purification.

Yield: 464 mg crude product

EXAMPLE 38A 4-tert-Butyl-N-[1-(3-cyclopentyl-5-oxo-4,5-dihydro-1,2,4-triazin-6-yl)propyl]cyclohexanecarboxamide

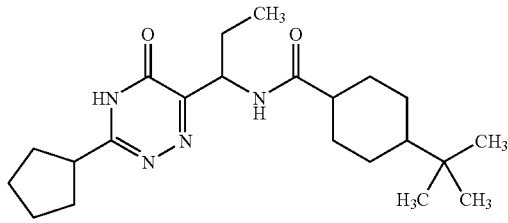

In analogy to the procedure for Example 36A, 200 mg (0.90 mmol) 6-(1-aminopropyl)-3-cyclopentyl-1,2,4-triazin-5(4H)-one, 180 mg (0.90 mmol) 4-tert-butylcyclohexanecarbonyl chloride and proportionate amounts of the other reagents are used. The crude product is used in the next step without further purification.

Yield: 350 mg crude product

EXAMPLE 39A 4-tert-Butyl-N-[1-(3-tert-butyl-5-oxo-4,5-dihydro-1,2,4-triazin-6-yl)propyl]cyclohexanecarboxamide

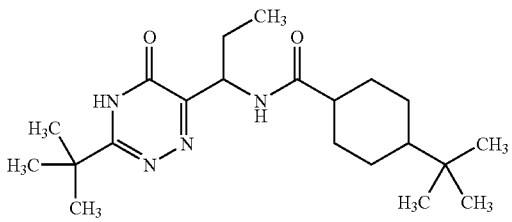

In analogy to the procedure for Example 36A, 210 mg (1.00 mmol) 6-(1-aminopropyl)-3-tert-butyl-1,2,4-triazin-5(4H)-one, 200 mg (1.00 mmol) 4-tert-butylcyclohexanecarbonyl chloride and proportionate amounts of the other reagents are used. The crude product is used in the next step without further purification.

Yield: 377 mg crude product

EXAMPLE 40A 4-tert-Butyl-N-[1-(5-oxo-3-phenyl-4,5-dihydro-1,2,4-triazin-6-yl)propyl]cyclohexanecarboxamide

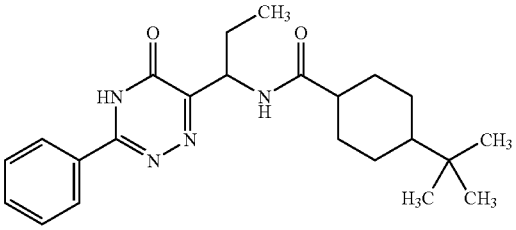

In analogy to the procedure for Example 36A, 100 mg (0.43 mmol) of Example 34A, 100 mg (0.48 mmol) 4-tert-butylcyclohexanecarbonyl chloride and proportionate amounts of the other reagents are used. A mixture of isomers is obtained.

Yield: 150 mg (87%) LC/MS (A): MS (ESI): 397 (M+H$^+$), retention time 4.14 min.

EXAMPLE 41A cis-4-tert-Butyl-N-{1-[3-(1-naphthyl)-5-oxo-4,5-dihydro-1,2,4-triazin-6-yl]propyl}-cyclohexanecarboxamide

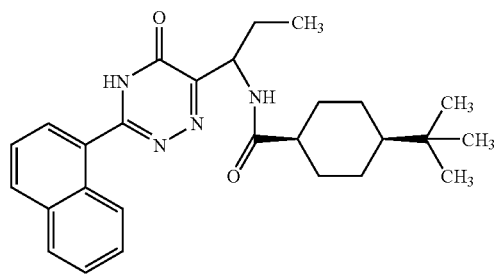

To a solution of 252 mg (1.37 mmol) cis-4-tert-butylcyclohexanecarboxylic acid and 185 mg (1.37 mmol) 1-hydroxy-1H-benzotriazol in 9 ml dichloromethane and 1 ml DMF was added at 0° C. first 0.23 ml N-ethyldiisopropylamine and then 300 mg (0.91 mmol) of Example 35A. After 10 minutes the solution was allowed to warm up to room temperature and stirred over night. The solution was diluted with dichloromethane and washed twice with 1N HCl solution and then with 5% sodium bicarbonate solution. The organic phase was dried over sodium sulfate, filtered and evaporated to dryness. The residue was purified by preparative HPLC.

Yield: 215 mg (53%) $^1$H-NMR (DMSO-d$_6$, 200 MHz): δ=0.8 (s, 9H), 1.0 (t, 3H), 1.2–2.2 (m, 12H), 5.0 (m, 1H), 7.5–8.3 (m, 8H), 14.1 (br. s, 1H) ppm.

EXAMPLE 42A cis-4-tert-Butylcyclohexanecarboxylic acid

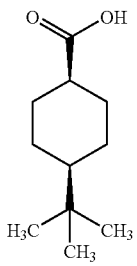

A preparative HPLC separation of cis- and trans-4-tert-butylcyclohexanecarboxylic acid was carried out under the following conditions:

| | |
|---|---|
| Feed: | 10 g isomeric mixture of cis- and trans-4-tert-butyl-cyclohexanecarboxylic acid dissolved in 500 ml iso-hexane (80%)/tert-butylmethylether (20%) |
| Column: | 330 × 100 mm; Self Packing Device NW 100; Merck |
| Stationary phase: | LiChrospher Si 60, 12 μm, Merck |
| Mobile phase: | iso-hexane/tert-butylmethylether (4/1 v/v) + 0.25 vol-% acetic acid |

-continued

| | |
|---|---|
| Flow: | 150 ml/min |
| Injection volume: | 70 ml (= 1.4 g compound) |
| Wave length: | 210 nm |
| Temperature: | 25° C. |

The sample run on this column was repeatedly injected every 30 minutes. The cis-isomer is the first eluting compound.

cis-isomer:
mp: 118° C. $^1$H-NMR (300 MHz, DMSO): δ=0.9 (t, 3 H), 1.0 (m, 3 H), 1.4 (m, 2 H), 1.6 (m, 1H), 2.1 (m, 2 H), 2.5 (m, 1 H), 12.0 (s, 1 H) ppm.

trans-isomer:
mp: 172° C. $^1$H-NMR (300 MHz, DMSO): δ=0.9 (t, 3 H), 1.0 (m, 3 H), 1.3 (m, 2 H), 1.7 (m, 1 H), 1.9 (m, 2 H), 2.1 (m, 1 H), 11.9 (s, 1 H) ppm.

EXAMPLE 43A cis-4-tert-Butylcyclohexanecarbonyl Chloride

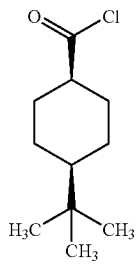

2.0 g (10.85 mmol) cis-4-tert-Butylcyclohexanecarboxylic acid (Example 42A) are dissolved in 50 ml dichloromethane, 1.65 g (13.02 mmol) ethanedioyl dichloride are added and the solution is stirred at room temperature for one hour. The mixture is then stirred at reflux for two hours and, after cooling down to room temperature, evaporated to dryness in vacuo. The residue is then dissolved in toluene two times and again evaporated to dryness in vacuo. The residue is used in the next step without further purification.

EXAMPLE 44A

4-Nitrobenzenecarboximidamide hydrochloride

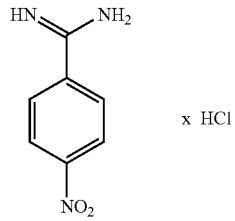

In analogy to the procedure for Example 3A, 10.0 g (67.5 mmol) 4-nitrobenzonitrile and proportionate amounts of the other reagents are used.

Yield: 12.64 g (93%) $^1$H-NMR (DMSO-d$_6$, 200 MHz): δ=8.1 (m, 2H), 8.4 (m, 2H) ppm.

EXAMPLE 45A

3-Cyanobenzenecarboximidamide hydrochloride

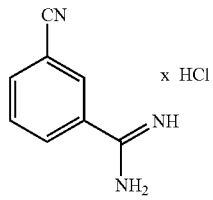

In analogy to the procedure for Example 3A, 20.0 g (125.9 mmol) 3-cyanobenzoic acid and proportionate amounts of the other reagents are used.

Yield: 4.27 g (17%) $^1$H-NMR (DMSO-d$_6$, 300 MHz): δ=7.8 (m, 1H), 8.1(m, 1H), 8.2 (m, 1H), 8.3 (m, 1H), 9.4 (br. s, 4H) ppm.

EXAMPLE 46A

N-{1-[3-(4-Methylphenyl)-5-oxo-4,5-dihydro-1,2,4-triazin-6-yl]propyl}acetamide

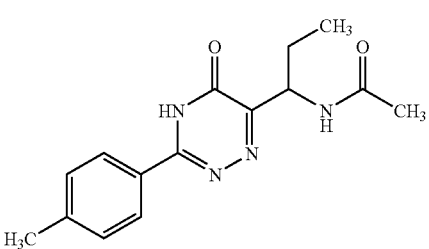

In analogy to the procedure for Example 10A, 3.0 g (17.6 mmol) 4-methylbenzenecarboximidamide hydrochloride and proportionate amounts of the other reagents are used.

Yield: 2.74 g (54%) $^1$H-NMR (DMSO-d$_6$, 400 MHz): δ=0.9 (t, 3H), 1.6 (m, 1H), 1.9 (m, 1H; s, 3H), 2.4 (s, 3H), 4.9 (m, 1H), 7.4 (m, 2H), 7.9 (m, 2H), 14.0 (s, 1H) ppm.

EXAMPLE 47A

N-{1-[3-(4-Nitrophenyl)-5-oxo-4,5-dihydro-1,2,4-triazin-6-yl]propyl}acetamide

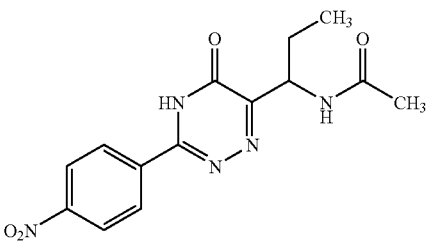

In analogy to the procedure for Example 10A, 7.29 g (36.16 mmol) of Example 44A and proportionate amounts of the other reagents are used.

Yield: 3.35 g (29%) $^1$H-NMR (DMSO-d$_6$, 400 MHz): δ=0.9 (t, 3H), 1.6 (m, 1H), 1.9 (m, 1H; s, 3H), 5.0 (m, 1H), 8.1 (d, 1H), 8.3 (m, 2H), 8.4 (m, 2H) ppm.

EXAMPLE 48A

N-{1-[3-(3-Cyanophenyl)-5-oxo-4,5-dihydro-1,2,4-triazin-6-yl]propyl}acetamide

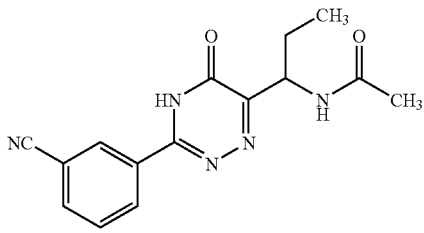

In analogy to the procedure for Example 10A, 4.27 g (23.5 mmol) of Example 45A and proportionate amounts of the other reagents are used.

Yield: 2.41 g (34%) $^1$H-NMR (DMSO-$d_6$, 300 MHz): δ=0.9 (t, 3H), 1.6 (m, 1H), 1.9 (m, 1H; s, 3H), 4.9 (m, 1H), 7.8 (m, 1H), 8.1 (m, 2H), 8.3 (m, 1H), 8.4 (m, 1H), 14.2 (br.s, 1H) ppm.

EXAMPLE 49A 6-(1-Aminopropyl)-3-(4-methylphenyl)-1,2,4-triazin-5(4H)-one

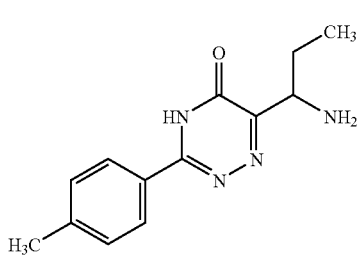

In analogy to the procedure for Example 23A, 2.74 g (9.57 mmol) of Example 46A and proportionate amounts of the other reagents are used. The product is used in the next step without further purification.

$^1$H-NMR (DMSO-$d_6$, 300 MHz): δ=0.9 (t, 3H), 1.8 (m, 1H), 1.9 (m, 1H), 2.3 (s, 3H), 4.1 (d/d, 1H), 7.2 (m, 2H), 8.1 (m, 2H) ppm.

EXAMPLE 50A 6-(1-Aminopropyl)-3-(4-nitrophenyl)-1,2,4-triazin-5(4H)-one

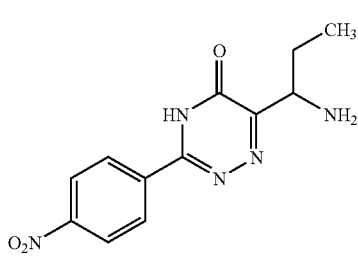

In analogy to the procedure for Example 23A, 3.33 g (10.51 mmol) of Example 47A and proportionate amounts of the other reagents are used.

Yield: 1.29 g (45%) LC/MS (A): MS (ESI): 276 (M+H$^+$), retention time 0.49 min.

EXAMPLE 51A

3-[6-(1-Aminopropyl)-5-oxo-4,5-dihydro-1,2,4-triazin-3-yl]benzonitrile

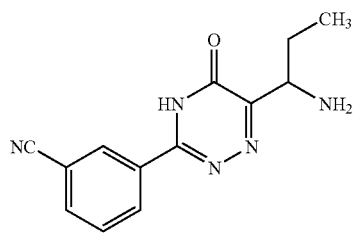

In analogy to the procedure for Example 23A, 2.41 g (8.11 mmol) of Example 48A and proportionate amounts of the other reagents are used.

Yield: 1.1 g (53%) LC/MS (A): MS (ESI): 256 (M+H$^+$), retention time 1.27 min.

EXAMPLE 52A 4-tert-Butyl-N-{1-[3-(4-methylphenyl)-5-oxo-4,5-dihydro-1,2,4-triazin-6-yl]propyl}cyclohexanecarboxamide

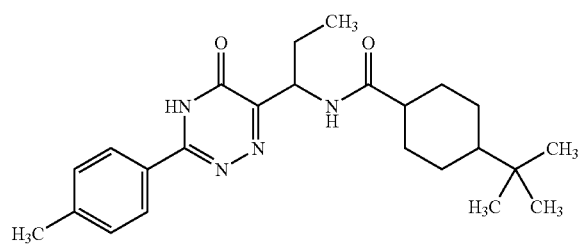

In analogy to the procedure for Example 37A, 800 mg (3.27 mmol) of Example 49A, 730 mg (3.60 mmol) 4-tert-butylcyclohexanecarbonyl chloride and proportionate amounts of the other reagents are used. The product is used in the next step without further purification.

LC/MS (A): MS (ESI): 411 (M+H$^+$), retention time 3.09 min.

EXAMPLE 53A cis-7-(4-tert-Butylcyclohexyl)-4-chloro-5-ethyl-2-(4-nitrophenyl)imidazo[5,1-f]-[1,2,4]triazine

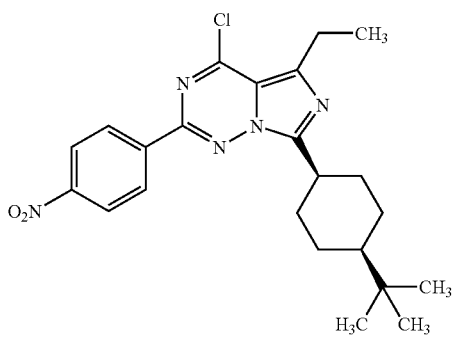

500 mg (1.82 mmol) of Example 50A are suspended in 20 ml dichloroethane, and 276 mg (2.72 mmol) triethylamine and 552 mg (2.72 mmol) cis-4-tert-butyl-cyclohexanecarbonyl chloride are added. The mixture is stirred at room temperature for one hour, then 279 mg (1.82 mmol) phosphoroxychloride are added. The mixture is stirred at reflux for 3 hours. After cooling down to room temperature, ethyl acetate and saturated NaHCO₃ (aq) are added. The organic phase is washed with saturated NaHCO₃ (aq), water and brine, dried over sodium sulfate and evaporated to dryness in vacuo. The product is purified by chromatography.

Yield: 127 mg (16%) cis-product MS (ESI): 442, 444 (M+H⁺).

EXAMPLE 54A cis-4-tert-Butyl-N-[1-(5-oxo-3-phenyl-4,5-dihydro-1,2,4-triazin-6-yl)propyl]cyclohexanecarboxamide

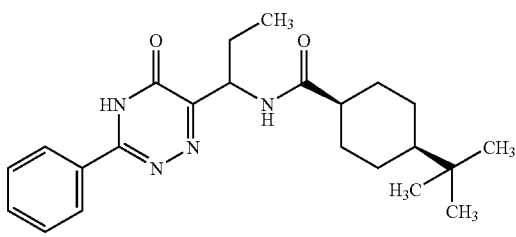

1.3 g (5.65 mmol) of Example 34A are suspended in 50 ml 1,2-dichloroethane, 0.94 ml (6.78 mmol) triethylamine and 1.26 g (6.21 mmol) cis-4-tert-butyl-cyclohexanecarbonyl (Example 43A) chloride are added. The reaction mixture is stirred at room temperature overnight. The reaction mixture is diluted with dichloromethane, washed with saturated sodium bicarbonate, the organic phase is dried over magnesium sulfate, filtered and evaporated to dryness.

Yield: 2.2 g (98.3%) LC/MS: MS (ESI): 397 (M+H⁺), retention time 4.14 min.

PREPARATION EXAMPLES

EXAMPLE 1

2-(3-Bromophenyl)-7-(4-tert-butylcyclohexyl)-5-ethylimidazo[5,1-f][1,2,4]triazin-4(3H)-one

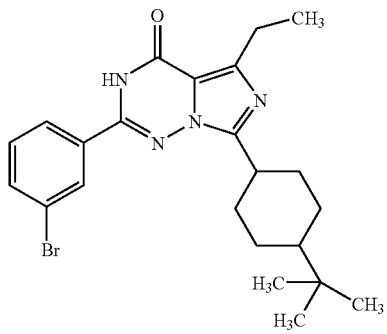

770 mg (1.62 mmol, 1 equiv.) of Example 36A are suspended in 70 ml dichloroethane, and 373 mg (2.45 mmol, 1.5 equiv.) phosphoroxychloride are added. The mixture is stirred at reflux for 3 hours. Then another 373 mg of phosphoric trichloride are added, and stirring at reflux is continued over night. After cooling down to room temperature, ethyl acetate and saturated NaHCO₃ (aq) are added. The organic phase is washed with saturated NaHCO₃ (aq), water and brine, dried over sodium sulfate and evaporated to dryness in vacuo. The product is purified and the isomers are separated by chromatography (flash or column chromatography or preparative HPLC).

Yield: 156 mg (21%) cis-isomer ¹H-NMR (DMSO-d₆, 300 MHz): δ=0.8 (s, 9H), 1.1 (m, 2H), 1.2 (t, 3H), 1.5 (m, 2H), 1.7 (m, 2H), 2.2 (m, 2H), 2.9 (q, 2H), 3.5 (m, 1H), 7.5 (m, 1H), 7.8 (m, 1H), 8.0 (m, 1H), 8.1 (m, 1H), 11.8 (s, 1H) ppm.

EXAMPLE 2

7-(4-tert-Butylcyclohexyl)-2-cyclopropyl-5-ethylimidazo[5,1-f][1,2,4]triazin-4(3H)-one

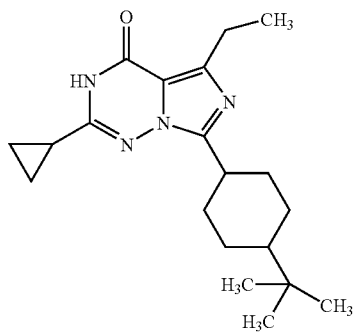

In analogy to the procedure for Example 1, 464 mg (1.29 mmol) crude 4-tert-butyl-N-[1-(3-cyclopropyl-5-oxo-4,5-dihydro-1,2,4-triazin-6-yl)propyl]cyclohexanecarboxamide, 200 mg (1.29 mmol) phosphoric trichloride are stirred at reflux for 3 hours, and proportionate amounts of the solvents are used. The resulting mixture is separated into the isomers via silica gel chromatography with eluent cyclohexane/ethylacetate 5/1, 2/1.

Yield: 20 mg (4.5%) cis-isomer ¹H-NMR (200 MHz, DMSO-d₆): δ=0.82 (s, 9H), 0.93–1.11 (m, 5H), 1.18 (t, 3 H), 1.44–2.18 (m, 9 H), 2.83 (q, 2 H), 3.33 (m, 1 H), 11.62 (s, 1H, NH) ppm.

EXAMPLES 3 AND 4

2-tert-Butyl-7-(4-tert-butylcyclohexyl)-5-ethylimidazo[5,1-f][1,2,4]triazin-4(3H)-one

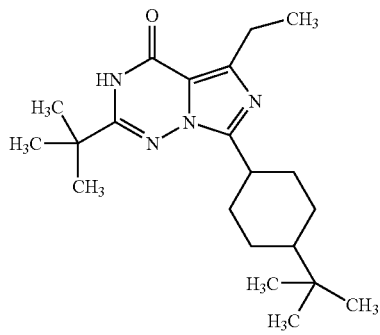

In analogy to the procedure for Example 1, 377 mg (1.00 mmol) crude 4-tert-butyl-N-[1-(3-tert-butyl-5-oxo-4,5- dihydro-1,2,4-triazin-6-yl)propyl]cyclohexanecarboxamide, 184 mg (1.20 mmol) phosphoric trichloride are stirred at reflux for 3 hours, proportionate amounts of the solvents are used. The resulting mixture is separated into the pure cis- and trans-isomers via silica gel chromatography with eluent cyclohexane/ethylacetate 10/1, 5/1.

Yield: 22 mg (6.13%) cis-isomer (Example 3) $^1$H-NMR (200 MHz, DMSO-d$_6$): δ=0.82 (s, 9 H), 0.95–1.12 (m, 1 H), 1.18 (t, 3 H), 1.28 (s, 9 H), 1.46–1.72 (m, 6 H), 2.09–2.23 (m, 2 H), 2.85 (q, 2 H), 3.43 (m, 1 H), 11.22 (s, 1 H, NH) ppm.

Yield: 60 mg (17%) trans-isomer (Example 4) $^1$H-NMR (200 MHz, DMSO-d$_6$): δ=0.87 (s, 9 H), 0.93–1.12 (m, 3 H), 1.18 (t, 3 H), 1.03 (s, 9 H), 1.48–2.07 (m, 6 H), 2.83 (q, 2 H), 2.98 (m, 1 H) ppm.

EXAMPLES 5 AND 6

7-(4-tert-Butylcyclohexyl)-2-cyclopentyl-5-ethylimidazo[5,1-f][1,2,4]triazin-4(3H)-one

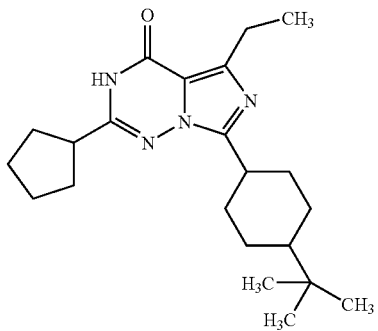

In analogy to the procedure for Example 1, 350 mg (0.90 mmol) crude 4-tert-butyl-N-[1-(3-cyclopentyl-5-oxo-4,5-dihydro-1,2,4-triazin-6-yl)propyl]cyclohexanecarboxamide, 140 mg (0.90 mmol) phosphoric trichloride are stirred at reflux for 3 hours, proportionate amounts of the solvents are used. The isomers are separated by chromatography.

Yield: 21 mg (6.3%) cis-isomer (Example 5) $^1$H-NMR (200 MHz, DMSO-d$_6$): δ=0.82 (s, 9 H), 0.98–1.12 (m, 1 H), 1.18 (t, 3 H), 1.44–2.01 (m, 14 H), 2.05–2.20 (m, 2 H), 2.77–2.98 (m, 3 H), 3.40 (m, 1 H) ppm.

Yield: 31 mg (17%) trans-isomer (Example 6) $^1$H-NMR (200 MHz, DMSO-d$_6$): δ=0.86 (s, 9H), 1.03–1.26 (m, 5 H, t at 1.17), 1.45–2.18 (m, 14 H), 2.74–3.03 (m, 3H) ppm.

EXAMPLES 7 AND 8

7-(4-tert-Butylcyclohexyl)-5-ethyl-2-phenylimidazo[5,1-f][1,2,4]triazin-4(3H)-one

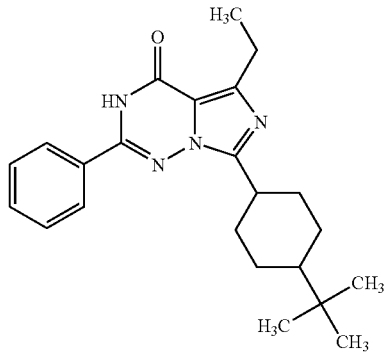

Method a)

In analogy to the procedure for Example 1, 150 mg (0.39 mmol) of Example 40A, 250 mg (1.61 mmol) phosphoric trichloride are stirred at reflux for 3 hours, proportionate amounts of the solvents are used. The isomers are separated by chromatography.

Yield: 26 mg (18%) trans-isomer (Example 7) $^1$H-NMR (300 MHz, DMSO): δ=0.87 (s, 9 H), 1.03–1.28 (m, 3 H), 1.23 (t, 3 H), 1.52–1.72 (m, 2 H), 1.78–1.93 (m, 2 H), 1.99–2.10 (m, 2 H), 2.90 (q, 2 H), 3.07–3.21 (m, 1 H), 7.51–7.67 (m, 3 H), 7.93–8.02 (m, 2 H), 11.95 (s, 1 H) ppm.

Yield: 11 mg (8%) cis-isomer (Example 8) $^1$H-NMR (300 MHz, DMSO): δ=0.83 (s, 9 H), 1.00–1.16 (m,1 H), 1.22 (t, 3 H), 1.44–1.79 (m, 6 H), 2.11–2.23 (m, 2 H), 2.90 (q, 2 H), 3.49–3.59 (m, 1 H), 7.47–7.60 (m, 3 H), 7.91–7.98 (m, 2 H) ppm.

Method b) for the Preparation of Example 8

7-(cis-4-tert-Butylcyclohexyl)-5-ethyl-2-phenylimidazo[5,1-f][1,2,4]triazin-4(3H)-one

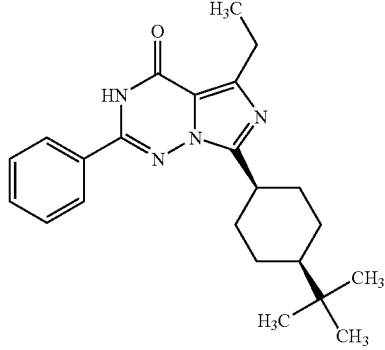

2.2 g (5.55 mmol, 1 equiv.) of Example 54A are suspended in 50 ml dichloroethane, and 3.62 g (23.2 mmol, 4 equiv.) phosphoroxychloride are added. The mixture is stirred at reflux for 4 hours. After cooling down to room temperature, dichloromethane is added and the organic phase is quenched with water, washed with water, dried over magnesium sulfate, and evaporated to dryness in vacuo. The solid residue is washed with diethyl ether, filtered and dried.

Yield: 1.02 g (49%) $^1$H-NMR identical with above (see method a).

Method c) for the Preparation of Example 8

20.45 g (0.09 mol) 6-(1-Aminopropyl)-3-phenyl-1,2,4-triazin-5(4H)-one (Example 34A) are dissolved in dichloroethane, 502 g (5.08 mol) triethylamine and 19.8 g (0.10 mol) cis-4-tert-butylcyclohexanecarbonyl chloride are added. The solution is stirred at reflux for three hours, then 20.42 g (0.13 mol) phosphoroxychloride are added. The solution is stirred at reflux for another 4 hours and, after cooling down to room temperature, water, sodium hydroxide and then dichloromethane are added. The organic phase is evaporated to dryness in vacuo, and the residue triturated with diethylether and filtrated. The solid is dissolved in methanol (75%)/dichloromethane (25%), the dichloromethane is evaporated in vacuo, and the crystallized product is filtered and dried.

Yield: 17.8 g (52%) $^1$H-NMR identical with above (see method a).

EXAMPLE 9

7-(cis-4-tert-Butylcyclohexyl)-5-ethyl-2-(1-naphthyl)imidazo[5,1-f][1,2,4]triazin-4(3H)-one

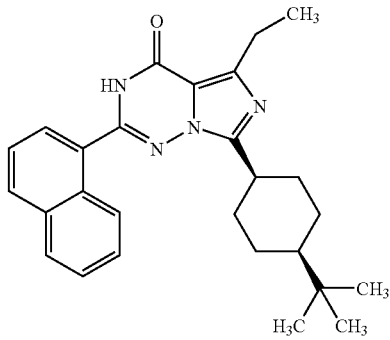

A solution of 200 mg (0.45 mmol) of Example 41A and 104 mg (0.67 mmol) phosphoric trichloride in 10 ml 1,2-dichloroethane is stirred at reflux for 4 hours. After work-up analogously to the procedure given for Example 1, the product was obtained as a solid.

Yield: 172 mg (89%) Melting point: 203° C. $^1$H-NMR (DMSO-d$_6$, 200 MHz): δ=11.9 (s, 1H), 8.3–7.5 (m, 7H), 3.5 (m, 1H), 2.9 (q, J=7.5 Hz, 2H), 2.1 (m, 2H), 1.7–1.5 (m, 6H), 1.3 (t, J=7.5 Hz, 3H), 1.0 (m, 1H), 0.8 (s, 9H) ppm.

EXAMPLE 10

7-(cis-4-tert-Butylcyclohexyl)-5-ethyl-2-(4-methylphenyl)imidazo[5,1-f][1,2,4]-triazin-4(3H)-one

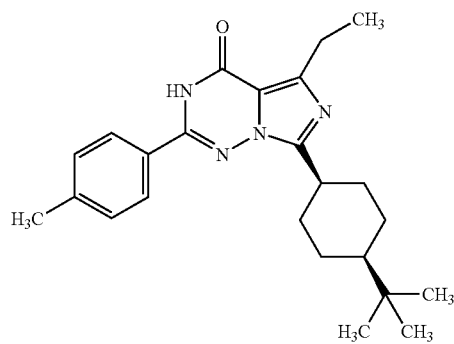

In analogy to the procedure for Example 1, 1750 mg (4.26 mmol) of Example 52A, 980 mg (6.39 mmol) phosphoric trichloride are stirred at reflux over night, proportionate amounts of the solvents are used.

Yield: 40 mg (2%) $^1$H-NMR (DMSO-d$_6$, 300 MHz): δ=0.8 (t, 9H), 1.1 (m, 1H), 1.2 (t, 3H), 1.6 (m, 6H), 2.2 (m, 2H), 2.4 (s, 3H), 2.9 (q, 2H), 3.5 (m, 1H), 7.4 (m, 2H), 7.9 (m, 2H), 11.7 (s, 1H) ppm.

EXAMPLE 11

7-(cis-4-tert-Butylcyclohexyl)-5-ethyl-2-(4-nitrophenyl)imidazo[5,1-f][1,2,4]triazin-4(3H)-one

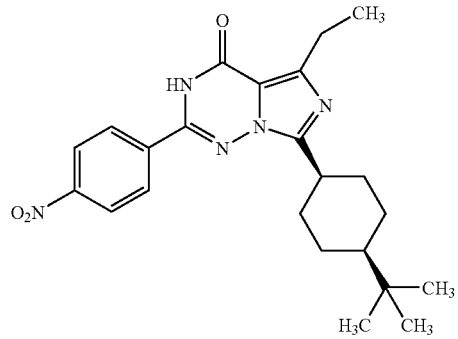

598 mg (1.35 mmol) of Example 53A are suspended in methanol, and 10 ml sodium hydroxide (10% in water) are added. The mixture is stirred at reflux over night. After cooling down to room temperature, the methanol is evaporated in vacuo, the residue dissolved in ethyl acetate, the organic phase washed with water and brine, dried over sodium sulfate and evaporated to dryness in vacuo.

Yield: 580 mg (quant.) $^1$H-NMR (DMSO-d$_6$, 300 MHz): δ=0.8 (s, 9H), 1.1 (m, 1H), 1.2 (t, 3H), 1.5–1.7 (m, 6H), 2.2 (m, 2H), 2.9 (q, 2H), 3.6 (m, 1H), 8.2 (m, 2H), 8.4 (m, 2H), 12.1 (s, 1H) ppm.

EXAMPLES 12 AND 13

7-(4-tert-Butylcyclohexyl)-5-ethyl-2-(3-fluorophenyl)imidazo[5,1-f][1,2,4]triazin-4(3H)-one

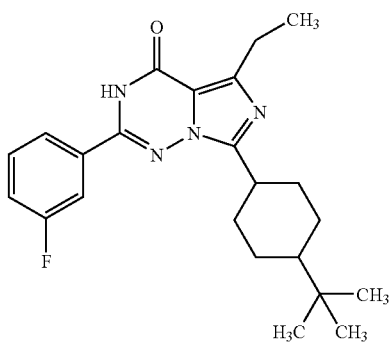

500 mg (2.01 mmol) of Example 25A are suspended in 20 ml dichloroethane, and 306 mg (3.02 mmol) triethylamine and 408 mg (2.01 mmol) 4-tert-butyl-cyclohexanecarbonyl chloride are added. The mixture is stirred at room temperature for one hour, then 463 mg (3.02 mmol) phosphoroxychloride are added. The mixture is stirred at reflux for 3 hours. After cooling down to room temperature, ethyl acetate and saturated NaHCO$_3$ (aq) are added. The organic phase is washed with saturated NaHCO$_3$ (aq), water and brine, dried over sodium sulfate and evaporated to dryness in vacuo. The product is purified by chromatography.

Yield: 33 mg (4%) cis-product (Example 12) $^1$H-NMR (DMSO-d$_6$, 200 MHz): δ=0.8 (s, 9H), 1.0 (m, 1H), 1.2 (t, 3H), 1.5–1.7 (m, 6H), 2.2 (m, 2H), 2.9 (q, 2H), 3.6 (m, 1H), 7.5 (m, 1H), 7.6 (m, 1H), 7.8 (m, 2H), 12.0 (br.s, 1H) ppm.

Yield: 29 mg (4%) trans-product (Example 13) $^1$H-NMR (DMSO-d$_6$, 200 MHz): δ=0.8 (s, 9H), 1.1 (m, 1H), 1.2 (t, 3H), 1.6 (m, 4H), 1.9 (m, 2H), 2.0 (m, 2H), 2.9 (q, 2H), 3.1 (m, 1H), 7.5 (m, 1H), 7.6 (m, 1H), 7.8 (m, 2H) ppm.

EXAMPLE 14 cis-3-[7-(4-tert-Butylcyclohexyl)-5-ethyl-4-oxo-3,4-dihydroimidazo[5,1-f][1,2,4]-triazin-2-yl]benzonitrile

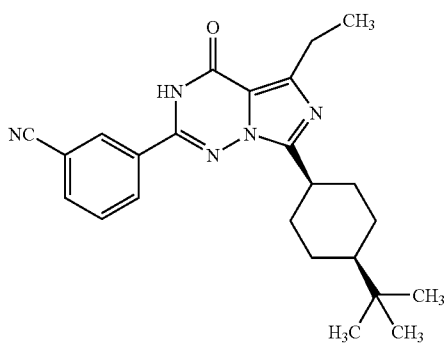

In analogy to the procedure for Examples 12 and 13. 1.09 g (4.27 mmol) of Example 51A, 0.86 g (4.27 mmol) cis-4-tert-butylcyclohexanecarbonyl chloride and proportionate amounts of the other reagents are used.

Yield: 0.70 g (41%) $^1$H-NMR (DMSO-d$_6$, 300 MHz): δ=0.8 (s, 9H), 1.1 (m, 1H), 1.2 (t, 3H), 1.5–1.7 (m, 6H), 2.2 (m, 2H), 2.9 (q, 2H), 3.6 (m, 1H), 7.7 (m, 1H), 8.0 (m, 1H), 8.3 (m, 1H), 8.4 (m, 1H), 11.9 (s, 1H) ppm.

We claim:
1. A compound of the general formula (I),

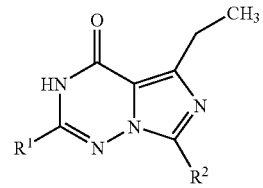

in which

R$^1$ denotes (C$_6$–C$_{10}$)-aryl, which is optionally substituted by identical or different residues selected from the group consisting of halogen, (C$_1$–C$_4$)-alkyl, trifluoromethyl, cyano, nitro and trifluoromethoxy, or denotes (C$_1$–C$_8$)-alkyl, which is optionally substituted by 3- to 10-membered carbocyclyl, or denotes 3- to 10-membered carbocyclyl, which is optionally substituted by identical or different (C$_1$–C$_4$)-alkyl residues, and R$^2$ denotes 4-tert-butyl-cyclohex-1-yl, or a salt, hydrate, or solvate thereof.

2. A compound according to claim 1, whereby

R$^1$ denotes naphthyl, or denotes phenyl, which is optionally substituted by identical or different halogen atoms.

3. A compound according to claim 1, whereby

R$^2$ denotes cis-4-tert-Butyl-cyclohex-1-yl.

4. A process for the preparation of a compound according to claim 1, characterized in that a compound of the general formula (IV),

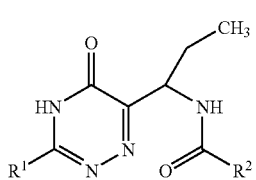

in which R$^1$ and R$^2$ have the meaning indicated in claim 1, in reacted with a dehydrating agent.

5. A compound of the general formula (IV)

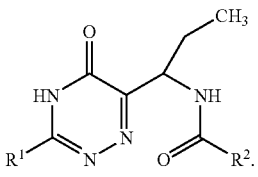

in which R$^1$ and R$^2$ have the meaning indicated in claim 1.

6. A pharmaceutical composition containing at least one compound according to claim 1 and a pharmacceutically acceptable diluent.

7. A method of treating chronic obstructive pulmonary disease or asthma, comprising administering to a mammal an effective amount of a compound according to claim 1.

8. The compound 7-(cis-4-tert-butylcyclohexyl)-5-ethyl-2-phenylimidazo[5,1-f][1,2,4]triazin-4(3H)-one:

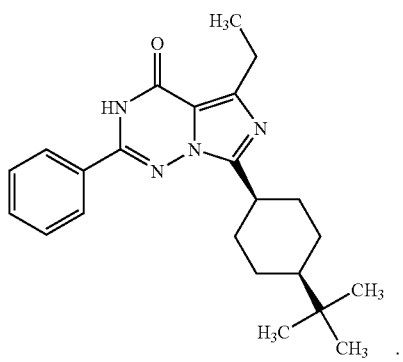

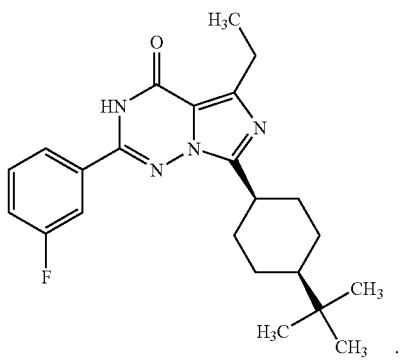

9. A method of treating chronic obstructive pulmonary disease or asthma, comprising administering to a mammal an effective amount of 7-(cis-4-tert-butylcyclohexyl)-5-ethyl-2-phenylimidazo[5,1-f][1,2,4]triazin-4(3H)-one.

10. A process for the preparation of 7-(cis-4-tert-butylcyclohexyl)-5-ethyl-2-phenylimidazo[5,1-f][1,2,4]triazin-4(3H)-one, comprising reacting cis-4-tert-butyl-N-[1-(5-oxo-3-phenyl-4,5-dihydro-1,2,4-triazin-6-yl)propyl]cyclo-hexanecarboxamide with phosphoroxychloride.

11. The compound 7-(cis-4-tert-butylcyclohexyl)-5-ethyl-2-(3-fluorophenyl)imidazo [5,1-f][1,2,4]triazin-4(3H)-one:

12. A method of treating chronic obstructive pulmonary disease or asthma, comprising administering to a mammal an effective amount of 7-(cis-4-tert-butylcyclohexyl)-5-ethyl-2-(3-fluorophenyl)imidazo [5,1-f][1,2,4]triazin-4(3H)-one.

13. A process for the preparation of 7-(cis-4-tert-butylcyclohexyl)-5-ethyl-2-(3-fluorophenyl)imidazo[5,1-f][1,2,4]triazin-4(3H)-one, comprising reacting 6-(1-aminopropyl)-3-(3-fluorophenyl)-1,2,4-triazin-5(4H)-one with 4-tert-butyl-cyclohexanecarbonyl chloride and phosphoroxychloride.

* * * * *